(12) United States Patent
Jones, Jr. et al.

(10) Patent No.: US 11,717,434 B2
(45) Date of Patent: *Aug. 8, 2023

(54) MEDICAL DEVICE WITH AN OPENING SYSTEM

(71) Applicant: CONVATEC TECHNOLOGIES INC., Las Vegas, NV (US)

(72) Inventors: James Donald Jones, Jr., Bridgewater, NJ (US); Gary Oberholtzer, Bridgewater, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/240,274

(22) Filed: Apr. 26, 2021

(65) Prior Publication Data

US 2021/0244564 A1 Aug. 12, 2021

Related U.S. Application Data

(63) Continuation of application No. 15/768,433, filed as application No. PCT/US2016/057214 on Oct. 14, 2016, now Pat. No. 11,039,950.

(Continued)

(51) Int. Cl.
*A61F 5/44* (2006.01)
*A61F 5/443* (2006.01)
(Continued)

(52) U.S. Cl.
CPC ............ *A61F 5/4407* (2013.01); *A61F 5/441* (2013.01); *A61F 5/442* (2013.01); *A61F 5/443* (2013.01); *A61F 5/445* (2013.01)

(58) Field of Classification Search
CPC ........ A61F 5/4407; A61F 5/441; A61F 5/442; A61F 5/443; A61F 5/44
See application file for complete search history.

(56) References Cited

U.S. PATENT DOCUMENTS 2,520,831 A * 8/1950 Chincholl ............... A61F 5/445
604/335
2,875,451 A 3/1959 Stegeman
(Continued)

FOREIGN PATENT DOCUMENTS

CN 201423018 Y 3/2010
EP 1378218 A1 1/2004
(Continued)

OTHER PUBLICATIONS

US 10,806,622 B2, 10/2020, Hansen et al. (withdrawn)
(Continued)

*Primary Examiner* — Guy K Townsend
(74) *Attorney, Agent, or Firm* — Taft Stettinius & Hollister LLP; Ryan O. White; Derek B. Lavender

(57) ABSTRACT

A medical device according to certain embodiments generally includes a first wall, a second wall, and a first deformable reinforcing member. The first wall and the second wall are joined to one another such that a cavity is formed between the first wall and the second wall. The cavity has an outlet opening formed at a proximal end of the medical device. The first deformable reinforcing member is attached to the first wall, and is deformable by manual application of pressure to lateral edges of the first deformable reinforcing member so as to radially distend the outlet opening. The first deformable reinforcing member includes at least one first notch formed in at least one lateral edge thereof. Each notch is configured to receive a portion of a user's digit to facilitate manual application of pressure to said lateral edges.

20 Claims, 18 Drawing Sheets

Related U.S. Application Data

(60) Provisional application No. 62/241,716, filed on Oct. 14, 2015.

(51) Int. Cl.
*A61F 5/441* (2006.01)
*A61F 5/442* (2006.01)
*A61F 5/445* (2006.01)

(56) References Cited

U.S. PATENT DOCUMENTS

| | | | |
|---|---|---|---|
| 3,507,282 A | 4/1970 | Judy | |
| 3,655,118 A * | 4/1972 | Rinecker | A44B 18/00 383/62 |
| 3,724,461 A | 4/1973 | Eisenberg | |
| 3,825,005 A | 7/1974 | Fenton | |
| 3,941,133 A | 3/1976 | Chen | |
| 4,061,820 A | 12/1977 | Magid et al. | |
| 4,233,977 A * | 11/1980 | Mattson | A61F 5/4407 604/335 |
| 4,314,558 A | 2/1982 | Korpman | |
| 4,519,797 A | 5/1985 | Hall | |
| 4,676,851 A | 6/1987 | Scheibner et al. | |
| 4,691,371 A | 9/1987 | Derby | |
| 5,030,013 A | 7/1991 | Kramer | |
| 5,074,852 A | 12/1991 | Castellana et al. | |
| 5,174,659 A | 12/1992 | Laske | |
| 5,248,308 A | 9/1993 | Von Emster | |
| 5,545,154 A * | 8/1996 | Oberholtzer | A61F 5/443 604/336 |
| 5,662,758 A | 9/1997 | Hamilton et al. | |
| 5,672,163 A * | 9/1997 | Ferreira | A61F 5/441 604/333 |
| 5,676,466 A | 10/1997 | Lindenbeck | |
| 5,730,736 A | 3/1998 | Sawers et al. | |
| 5,745,926 A | 5/1998 | Cailleteau | |
| 5,843,054 A | 12/1998 | Honig | |
| 5,863,131 A | 1/1999 | Nakamura | |
| 5,871,607 A | 2/1999 | Hamilton et al. | |
| 5,965,235 A | 10/1999 | McGuire et al. | |
| 5,968,023 A | 10/1999 | Olsen | |
| 5,968,024 A | 10/1999 | Freeman | |
| 6,193,918 B1 | 2/2001 | McGuire et al. | |
| 6,267,506 B1 * | 7/2001 | Campion | A45C 11/22 383/89 |
| 6,336,918 B1 * | 1/2002 | Olsen | A61F 5/4407 604/355 |
| 6,419,664 B1 * | 7/2002 | von Bulow | A61F 5/4407 604/327 |
| 6,421,052 B1 | 7/2002 | McGuire | |
| 6,489,022 B1 | 12/2002 | Hamilton et al. | |
| 6,589,221 B1 * | 7/2003 | Olsen | A61F 5/4407 604/332 |
| 6,620,474 B1 | 9/2003 | Regnier et al. | |
| 6,726,667 B2 * | 4/2004 | Leise, Jr. | A61F 5/445 604/335 |
| 6,780,172 B2 * | 8/2004 | Olsen | A61F 5/4407 604/332 |
| 6,858,023 B2 * | 2/2005 | Poulsen | A61F 5/4407 604/335 |
| 6,887,222 B2 * | 5/2005 | Mandzij | A61F 5/4407 604/277 |
| 7,223,260 B2 * | 5/2007 | Hansen | A61F 5/4407 604/338 |
| 7,306,581 B2 * | 12/2007 | Falconer | A61F 5/4407 604/339 |
| 7,842,018 B2 * | 11/2010 | Schena | A61F 5/445 604/344 |
| 7,879,016 B2 * | 2/2011 | Mandzij | A61F 5/4407 4/144.1 |
| 7,947,025 B2 * | 5/2011 | Buglino | A61F 5/445 604/335 |
| 8,002,759 B2 | 8/2011 | Andersen et al. | |
| 8,206,364 B2 * | 6/2012 | Schertiger | A61F 5/4407 604/327 |
| 8,449,511 B2 * | 5/2013 | Andersen | A61F 5/443 604/326 |
| 8,449,513 B2 | 5/2013 | Abrams | |
| 8,500,707 B2 * | 8/2013 | Murray | A61F 5/445 383/88 |
| 8,672,907 B2 * | 3/2014 | Friske | A61F 5/4407 604/335 |
| 8,821,463 B2 * | 9/2014 | Grum-Schwensen | A61F 5/443 604/332 |
| 8,888,760 B2 * | 11/2014 | Andersen | A61F 5/44 604/335 |
| 8,905,987 B2 * | 12/2014 | Murray | A61F 5/445 383/57 |
| 8,979,811 B2 | 3/2015 | Keleny et al. | |
| 9,066,807 B2 | 6/2015 | Tsai et al. | |
| 9,629,744 B2 * | 4/2017 | Villefrance | A61F 5/4405 |
| 9,668,910 B2 * | 6/2017 | Murray | A61F 5/4407 |
| 9,968,480 B2 | 5/2018 | Nyberg | |
| 10,278,857 B2 | 5/2019 | Hansen et al. | |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 * | 10/2020 | Lysgaard | A61F 5/4404 |
| 10,813,787 B2 | 10/2020 | Dinakara et al. | |
| 11,039,950 B2 * | 6/2021 | Jones, Jr. | A61F 5/442 |
| 11,065,144 B2 * | 7/2021 | Nielsen | A61F 5/4407 |
| 11,076,978 B2 | 8/2021 | Nguyen-Demary et al. | |
| 11,076,979 B2 | 8/2021 | Fattman et al. | |
| 11,083,617 B2 | 8/2021 | Larsen | |
| 11,096,818 B2 | 8/2021 | Thirstrup et al. | |
| 11,191,662 B2 | 12/2021 | Cesa et al. | |
| 11,229,543 B2 | 1/2022 | Cesa et al. | |
| 11,246,739 B2 | 2/2022 | Ekfeldt et al. | |
| 11,291,579 B2 | 4/2022 | Hanuka et al. | |
| 11,351,055 B2 | 6/2022 | Jones et al. | |
| 11,357,658 B2 | 6/2022 | Cardell et al. | |
| 2002/0010444 A1 | 1/2002 | Wiltshire et al. | |
| 2003/0028160 A1 * | 2/2003 | Leise, Jr. | A61F 5/445 604/334 |
| 2003/0073962 A1 * | 4/2003 | Olsen | A61F 5/445 604/327 |

(56) References Cited

U.S. PATENT DOCUMENTS

| | | | |
|---|---|---|---|
| 2003/0167042 A1* | 9/2003 | Poulsen | A61F 5/4407 604/327 |
| 2004/0049837 A1* | 3/2004 | Falconer | A61F 5/4407 383/88 |
| 2004/0143230 A1 | 7/2004 | Hansen et al. | |
| 2004/0171999 A1* | 9/2004 | Andersen | A61F 5/445 604/332 |
| 2004/0267216 A1 | 12/2004 | Udayakumar et al. | |
| 2005/0131360 A1* | 6/2005 | Villefrance | A61F 5/445 604/332 |
| 2005/0159717 A1* | 7/2005 | Holtermann | A61F 5/4407 604/332 |
| 2006/0058576 A1 | 3/2006 | Davies et al. | |
| 2006/0111682 A1* | 5/2006 | Schena | A61F 5/442 604/334 |
| 2007/0265588 A1* | 11/2007 | Pedersen | A61F 5/4407 604/340 |
| 2008/0033379 A1* | 2/2008 | Pedersen | A61F 5/4407 604/335 |
| 2008/0051743 A1* | 2/2008 | Falconer | A61F 5/4407 604/277 |
| 2008/0097360 A1* | 4/2008 | Andersen | A61F 5/4407 604/332 |
| 2008/0226864 A1 | 9/2008 | Willis et al. | |
| 2009/0034882 A1 | 2/2009 | Chih et al. | |
| 2009/0082743 A1* | 3/2009 | Buglino | A61F 5/4405 604/335 |
| 2009/0143755 A1* | 6/2009 | Schertiger | A61F 5/445 29/428 |
| 2010/0152686 A1 | 6/2010 | Ryder et al. | |
| 2010/0174253 A1 | 7/2010 | Cline et al. | |
| 2011/0028923 A1* | 2/2011 | Murray | A61F 5/4405 604/332 |
| 2011/0028924 A1* | 2/2011 | Murray | A61F 5/4407 604/332 |
| 2011/0218507 A1 | 9/2011 | Andersen et al. | |
| 2012/0022477 A1* | 1/2012 | Grum-Schwensen | A61F 5/443 604/332 |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2013/0072886 A1 | 3/2013 | Schertiger et al. | |
| 2013/0226063 A1 | 8/2013 | Taylor et al. | |
| 2014/0005619 A1* | 1/2014 | Andersen | A61F 5/4404 604/332 |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 | 10/2014 | Ekfeldt et al. | |
| 2015/0133881 A1 | 5/2015 | Freiding | |
| 2015/0209172 A1 | 7/2015 | Richmann et al. | |
| 2016/0135983 A1 | 5/2016 | Murray | |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2017/0209297 A1* | 7/2017 | Lysgaard | A61F 5/4404 |
| 2018/0064572 A1 | 3/2018 | Wiltshire | |
| 2018/0235801 A1 | 8/2018 | Oellgaard et al. | |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0333290 A1* | 11/2018 | Jones | A61F 5/441 |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1* | 1/2019 | Grum-Schwensen | A61F 5/4407 |
| 2019/0110919 A1 | 4/2019 | Beckers et al. | |
| 2019/0117824 A1 | 4/2019 | Hansen et al. | |
| 2019/0247549 A1 | 8/2019 | Nielsen | |
| 2019/0328571 A1 | 10/2019 | Adachi | |
| 2019/0328572 A1* | 10/2019 | Weinberg | A61F 5/4407 |
| 2019/0365560 A1 | 12/2019 | Timms et al. | |
| 2019/0374372 A1 | 12/2019 | Seres et al. | |
| 2019/0380860 A1 | 12/2019 | Eggert et al. | |
| 2019/0380861 A1 | 12/2019 | Nordquist et al. | |
| 2019/0380882 A1 | 12/2019 | Taylor et al. | |
| 2020/0015996 A1 | 1/2020 | Schertiger | |
| 2020/0030134 A1 | 1/2020 | Hopper | |
| 2020/0038226 A1 | 2/2020 | Botten et al. | |
| 2020/0046541 A1 | 2/2020 | Sund et al. | |
| 2020/0046542 A1 | 2/2020 | Guidry et al. | |
| 2020/0046543 A1 | 2/2020 | Scalise et al. | |
| 2020/0054478 A1 | 2/2020 | Forsell | |
| 2020/0060863 A1 | 2/2020 | Sund et al. | |
| 2020/0061282 A1 | 2/2020 | Hvid et al. | |
| 2020/0069455 A1 | 3/2020 | Oberholtzer et al. | |
| 2020/0078206 A1 | 3/2020 | Chiladakis | |
| 2020/0100931 A1 | 4/2020 | Schoess et al. | |
| 2020/0100946 A1 | 4/2020 | Wohlgemuth et al. | |
| 2020/0138619 A1 | 5/2020 | Cisko, Jr. et al. | |
| 2020/0146944 A1 | 5/2020 | Moulton et al. | |
| 2020/0163792 A1 | 5/2020 | Schertiger | |
| 2020/0164196 A1 | 5/2020 | Jin et al. | |
| 2020/0188160 A1 | 6/2020 | Udayakumar | |
| 2020/0197213 A1 | 6/2020 | Frampton-Vallance et al. | |
| 2020/0214872 A1* | 7/2020 | Tretheway | A61F 5/443 |
| 2020/0214873 A1* | 7/2020 | Tretheway | A61F 5/4407 |
| 2020/0214875 A1* | 7/2020 | Tretheway | A61F 5/448 |
| 2020/0229962 A1* | 7/2020 | Torstensen | A61F 5/4407 |
| 2020/0246173 A1 | 8/2020 | Schertiger et al. | |
| 2020/0261254 A1 | 8/2020 | Williams et al. | |
| 2020/0276044 A1 | 9/2020 | Tretheway et al. | |
| 2020/0276045 A1 | 9/2020 | Bendavit | |
| 2020/0281758 A1 | 9/2020 | Tan | |
| 2020/0281761 A1* | 9/2020 | Tretheway | A61F 5/4404 |
| 2020/0289307 A1 | 9/2020 | Tretheway et al. | |
| 2020/0289308 A1 | 9/2020 | Tretheway et al. | |
| 2020/0297524 A1 | 9/2020 | Hunt et al. | |
| 2020/0306073 A1 | 10/2020 | Olsen et al. | |
| 2020/0306074 A1 | 10/2020 | Speiermann et al. | |
| 2020/0330258 A1 | 10/2020 | Hansen et al. | |
| 2020/0330259 A1 | 10/2020 | Sund et al. | |
| 2020/0330260 A1 | 10/2020 | Hansen et al. | |
| 2020/0337880 A1 | 10/2020 | Hansen et al. | |
| 2020/0337881 A1 | 10/2020 | Hansen et al. | |
| 2020/0337882 A1 | 10/2020 | Hansen et al. | |
| 2020/0337883 A1 | 10/2020 | Hansen et al. | |
| 2020/0338230 A1 | 10/2020 | Israelson et al. | |
| 2021/0244564 A1* | 8/2021 | Jones, Jr. | A61F 5/441 |
| 2021/0268142 A1 | 9/2021 | Lam et al. | |
| 2022/0000652 A1 | 1/2022 | Thirstrup et al. | |

FOREIGN PATENT DOCUMENTS

| | | | |
|---|---|---|---|
| EP | 3410993 B1 | 6/2021 | |
| EP | 2846746 B1 | 3/2022 | |
| EP | 3520826 B1 | 5/2022 | |
| EP | 3998052 A1 | 5/2022 | |
| EP | 2942039 B1 | 7/2022 | |
| GB | 2346328 A * | 8/2000 | A61F 5/4407 |
| GB | 2346328 A | 8/2000 | |
| GB | 2534012 A | 7/2016 | |
| GB | 2544180 A | 5/2017 | |
| GB | 2548673 A | 9/2017 | |
| GB | 2550936 A | 12/2017 | |
| JP | 2004130084 A | 4/2004 | |
| JP | 2006501002 A | 1/2006 | |
| JP | 2012522536 A | 9/2012 | |
| JP | 201386808 A | 5/2013 | |
| JP | 5486134 B2 | 5/2014 | |
| JP | 5593040 B2 | 9/2014 | |
| WO | 2006031275 A2 | 3/2006 | |
| WO | 2008134334 A1 | 11/2008 | |

(56) References Cited

FOREIGN PATENT DOCUMENTS

| | | | |
|---|---|---|---|
| WO | 2009124324 | A1 | 10/2009 |
| WO | 2010077377 | A1 | 7/2010 |
| WO | 2015110544 | A1 | 7/2015 |
| WO | 2015138190 | A1 | 9/2015 |
| WO | 2015148035 | A1 | 10/2015 |
| WO | 2017066701 | A1 | 4/2017 |
| WO | 2018188706 | A1 | 10/2018 |
| WO | 2018188707 | A1 | 10/2018 |
| WO | 2019058126 | A1 | 3/2019 |
| WO | 2019058127 | A1 | 3/2019 |
| WO | 2019091526 | A1 | 5/2019 |
| WO | 2019091527 | A1 | 5/2019 |
| WO | 2019091528 | A1 | 5/2019 |
| WO | 2019091529 | A1 | 5/2019 |
| WO | 2019091532 | A1 | 5/2019 |
| WO | 2019099662 | A1 | 5/2019 |
| WO | 2019120424 | A1 | 6/2019 |
| WO | 2019120429 | A1 | 6/2019 |
| WO | 2019120430 | A1 | 6/2019 |
| WO | 2019120432 | A1 | 6/2019 |
| WO | 2019120433 | A1 | 6/2019 |
| WO | 2019120434 | A1 | 6/2019 |
| WO | 2019120437 | A1 | 6/2019 |
| WO | 2019120438 | A1 | 6/2019 |
| WO | 2019120439 | A1 | 6/2019 |
| WO | 2019120442 | A1 | 6/2019 |
| WO | 2019120443 | A1 | 6/2019 |
| WO | 2019120444 | A1 | 6/2019 |
| WO | 2019120446 | A1 | 6/2019 |
| WO | 2019120448 | A1 | 6/2019 |
| WO | 2019120449 | A1 | 6/2019 |
| WO | 2019120450 | A1 | 6/2019 |
| WO | 2019120451 | A1 | 6/2019 |
| WO | 2019120452 | A1 | 6/2019 |
| WO | 2019120458 | A1 | 6/2019 |
| WO | 2019197291 | A1 | 10/2019 |
| WO | 2019197971 | A1 | 10/2019 |
| WO | 2019198012 | A1 | 10/2019 |

OTHER PUBLICATIONS

Chinese Office Action; The State Intellectual Property Office of the People's Republic of China; Chinese Application No. 201680073366.9; dated Dec. 30, 2019; 15 pages.
Japanese Office Action; Japanese Patent Office; Japanese Patent Application No. 2018-519416; dated Jul. 15, 2020; 16 pages.
Bangladesh Patent Application No. 255/2016 Office Action dated Oct. 9, 2017.
Canadian Patent Application No. 2,939,451 Office Action dated Oct. 31, 2017.
PCT/US2008/061212 International Preliminary Report on Patentability dated Oct. 27, 2009.
PCT/US2008/061212 International Search Report and Written Opinion dated Sep. 9, 2008.
PCT/US2009/039759 International Preliminary Report on Patentability dated Oct. 5, 2010.
PCT/US2009/039759 International Search Report and Written Opinion dated Jun. 4, 2010.
PCT/US2009/039764 International Preliminary Report on Patentability dated Oct. 5, 2010.
PCT/US2009/039764 International Search Report and Written Opinion dated Jun. 30, 2009.
PCT/US2016/057214 International Preliminary Report on Patentability dated Apr. 17, 2018.
PCT/US2016/057214 International Search Report and Written Opinion dated Dec. 23, 2016.
U.S. Appl. No. 12/450,715 Office Action dated Aug. 24, 2012.
U.S. Appl. No. 12/450,715 Office Action dated De. 5, 2011.
U.S. Appl. No. 12/936,249 Office Action dated May 2, 2012.
U.S. Appl. No. 14/4 79,178 Office Action dated Aug. 30, 2016.
U.S. Appl. No. 14/4 79,178 Office Action dated Mar. 21, 2016.
U.S. Appl. No. 14/723,246 Office Action dated Jan. 25, 2018.
U.S. Appl. No. 14/723,246 Office Action dated Aug. 13, 2018.
Chinese Office Action; The State Intellectual Property Office of the People's Republic of China; Chinese Application No. 201680073366.9; dated Apr. 2, 2021; 14 pages.
Chinese Office Action; The State Intellectual Property Office of the People's Republic of China; Chinese Application No. 201680073366.9; dated Jul. 29, 2021; 13 pages.

* cited by examiner

MEDICAL DEVICE WITH AN OPENING SYSTEM

CROSS-REFERENCE

This application is a continuation of U.S. patent application Ser. No. 15/768,433, which is a National Stage Entry of PCT/US16/57214, which claims the benefit of U.S. Provisional Application No. 62/241,716 filed Oct. 14, 2015, each of which is incorporated by reference herein in its entirety.

FIELD OF THE INVENTION

Disclosed within are opening systems for medical devices. The medical device is for collecting, storing and/or disposing of bodily fluids or waste. In certain embodiments, the medical device is an ostomy bag or pouch.

BACKGROUND OF THE INVENTION

Medical devices and ostomy pouches for the removal and storage of bodily fluids are used by many patients every day. Conditions that affect the bladder and digestive system can lead to the necessity of an ostomy, which is a temporary, or permanent, surgical creation of an opening, or stoma, from a part of the body such as the bladder or intestines to the outside of the body. There are many different types of ostomy such as colostomy, ileostomy or urostomy.

SUMMARY OF THE INVENTION

The present invention provides for improved methods to easily and reliably drain bodily waste from a reusable and drainable medical device such as an ostomy pouch. The features disclosed herein may permit users with limited dexterity and strength to manipulate, open and seal the drainable pouch.

Disclosed herein are medical devices, including ostomy pouches, comprising a closable opening for the storage, removal and sanitary disposal of waste and bodily fluids. In one embodiment is described a medical device with an opening system comprising (a) opposing walls having a cavity therebetween, the walls joined along their peripheries, and tapering to an outlet opening; (b) first and second deformable reinforcing members attached to opposing exterior surfaces of said opposing walls, wherein each reinforcing member has two lateral edges deformable by manual application of pressure to said lateral edges, so as to radially distend the outlet opening, wherein the first and second deformable reinforcing members are offset from each other along a longitudinal axis; and (c) first and second fasteners; wherein the outlet is flexible and foldable from an open condition to a closed condition by one or more folds. In some embodiments, the medical device with an opening system further comprises (d) a system for securing the device in the closed condition, the system comprising: a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; and wherein the first fastener is attached to the same exterior surface of one of said opposing walls as said first reinforcing member, distal to the opening with respect to said first reinforcing member, the second fastener is attached to the freely opened portion of said security flap, and wherein the first fastener and the second fastener are capable of forming a linkage when the outlet is in the closed condition. In some embodiments, at least one of the first and second fasteners is a hook and loop fastener. In some embodiments, the first deformable reinforcing member is near the outlet opening, and the second deformable reinforcing member is distal to the outlet opening with respect to the first deformable reinforcing member. In some embodiments, the second deformable reinforcing member is near the outlet opening, and the first deformable reinforcing member is distal to the outlet opening with respect to the second deformable reinforcing member. In some embodiments, the first and second deformable reinforcing members differ in size. In some embodiments, the first and second deformable reinforcing members differ in shape. In some embodiments, the lateral edges of the first and second reinforcing members are notched. In some embodiments, the lateral edges of the first and second reinforcing members are grooved, cut-to-shape or the like. In some embodiments, at least one of the first and second deformable reinforcing members extend the entire width of the outlet opening. In some embodiments, at least one of the first and second fasteners extends the entire width of the outlet opening. In some embodiments, the first and second fasteners differ in size and shape. In some embodiments, the first and second fastener form a linkage after at least two folds of the outlet from the open towards the closed position. In some embodiments, the first and second fastener form a linkage after two lateral folds of the outlet.

Another embodiment provides a medical device with an opening system comprising: (a) opposing walls having a cavity therebetween, the walls joined along their peripheries, and tapering to an outlet opening at the proximal end of the device; (b) a deformable reinforcing member on one exterior surface of said opposing walls, near the outlet opening, said reinforcing member having two lateral edges deformable by manual application of pressure to said lateral edges, so as to radially distend the outlet opening, wherein the lateral edge of the reinforcing member is notched, grooved, cut-to-shape or the like; and (c) a first fastener and a second fastener attached to opposing exterior surfaces of said opposing walls, wherein one of said first and second fastener is near the outlet opening; wherein the outlet is flexible and foldable from an opened condition to a closed condition by one or more folds, and wherein the first and second fastener are capable of forming a linkage when said outlet is in the closed condition. In some embodiments, the medical device further comprises a system for securing the device in the closed condition, the system comprising (d) a security flap, wherein said flap is attached to one exterior surface of said opposing walls, distal to the opening of the outlet with respect to said deformable reinforcing member, wherein a portion of the flap extends freely from said one exterior surface of said opposing wall to which the flap is attached; (e) a third fastener attached to one exterior surface of said opposing pouch walls, and (f) a fourth fastener attached to the freely opened portion of the security flap, wherein said third and fourth fastener can form a linkage when said outlet is in the closed condition. In some embodiments, at least one of the first, second, third and fourth fasteners is a hook and loop fastener. In some embodiments, the first fastener is attached to the deformable reinforcing member having two lateral edges and is deformable by manual application of pressure to said lateral edges, so as to controllably distend the outlet opening. In some embodiments, the second fastener is attached to the deformable reinforcing member having two lateral edges and is deformable by manual application of pressure to said lateral edges, so as to controllably distend the outlet opening. In some embodiments, at least one of the first, second, third, and fourth fasteners differs in shape with respect to any other fastener. In some embodiments, at least one of the first, second, third, and fourth fasteners differs in size with respect to any other fastener. In some embodiments, the first and second fasteners form a linkage after at least two folds of the outlet. In some embodiments, the third and fourth fasteners form a linkage after at least two folds of the outlet.

In another embodiment is provided an ostomy pouch comprising: (a) opposing walls having a cavity therebetween, the walls joined along their peripheries, and tapering to an outlet opening at the proximal end of the device; (b) first and second deformable reinforcing members attached to opposing exterior surfaces of said opposing walls, wherein each reinforcing member has two lateral edges deformable by manual application of pressure to said lateral edges, so as to radially distend the outlet opening, wherein the first and second deformable reinforcing members are offset from each other along a longitudinal axis; and (c) first and second fasteners; wherein the outlet is flexible and foldable from an open condition to a closed condition by one or more folds. In some embodiments, the ostomy pouch further comprises a system for securing the device in the closed condition, the system comprising: (d) a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; and wherein the first fastener is attached to the same exterior surface of one of said opposing walls as said first reinforcing member, distal to the opening with respect to said first reinforcing membrane, and the second fastener attached to the freely opened portion of said security flap, wherein the first fastener and the second fastener are capable of forming linkage when the outlet is in the closed condition. In some embodiments, at least one of the first and second fasteners is a hook and loop fastener. In some embodiments, the first deformable reinforcing member is near the outlet opening, and the second deformable reinforcing member is distal to the outlet opening with respect to the first deformable reinforcing member. In some embodiments, the second deformable reinforcing member is near the outlet opening, and the first deformable reinforcing member is distal to the outlet opening with respect to the second deformable reinforcing member. In some embodiments, the first and second deformable reinforcing members differ in size. In some embodiments, the first and second deformable reinforcing members differ in shape. In some embodiments, the lateral edges of the first and second reinforcing members have material removed to create corners with void space. In some embodiments, at least one of the first and second deformable reinforcing members extends the entire width of the outlet opening. In some embodiments, at least one of the first and second fasteners extends the entire width of the outlet opening. In some embodiments, the first and second fasteners differ in size. In some embodiments, the first and second fasteners differ in shape. In some embodiments, the first and second fastener form a linkage after two lateral folds of the outlet.

Another embodiment provides an ostomy pouch comprising: (a) opposing walls having a cavity therebetween, the walls joined along their peripheries and tapering to an outlet opening at the proximal end of the device; (b) a deformable reinforcing member on one exterior surface of said opposing walls, near the outlet, said reinforcing member having two lateral edges deformable by manual application of pressure to said lateral edges, so as to radially distend the outlet opening, wherein the lateral edge of the reinforcing member is notched, grooved, cut-to-shape or the like; and; (c) a first fastener and a second fastener attached to opposing exterior surfaces of said opposing walls, wherein one of said first and second fastener is near the outlet opening; wherein the outlet being flexible and foldable from an opened condition to a closed condition, and wherein the first and second fastener are capable of forming a linkage when said outlet is in the closed condition. In some embodiments, the ostomy pouch further comprises a system for securing the device in the closed condition, the system comprising: (d) a security flap, wherein said flap is attached to one exterior surface of said opposing walls, distal to the opening of the outlet with respect to said deformable reinforcing member, wherein a portion of the flap extends freely from said one exterior surface of said opposing wall to which the flap is attached; (e) a third fastener attached to one exterior surface of said opposing pouch walls, and (f) a fourth fastener attached to the freely opened portion of the security flap, wherein said third and fourth fastener can form a linkage when said outlet is in the closed condition. In some embodiments, at least one of the first, second, third and fourth fasteners is a hook and loop fastener. In some embodiments, the first fastener is attached to the deformable reinforcing member having two lateral edges and is deformable by manual application of pressure to said lateral edges, so as to controllably distend the outlet opening. In some embodiments, the second fastener is attached to the deformable reinforcing member having two lateral edges and is deformable by manual application of pressure to said lateral edges, so as to controllably distend the outlet opening. In some embodiments, at least one of the first, second, third, and fourth fasteners differ in shape with respect to the other fasteners. In some embodiments, at least one of the first, second, third, and fourth fasteners differ in size with respect to the other fasteners. In some embodiments, the first and second fasteners form a linkage after two lateral folds of the outlet. In some embodiments, the third and fourth fasteners form a linkage after two lateral folds of the outlet.

Another embodiment provides, a medical device with an opening system comprising: (a) opposing walls having a cavity therebetween, the walls joined along their peripheries, and tapering to an outlet opening at the proximal end of the device; (b) first and second deformable reinforcing members attached to opposing exterior surfaces of said opposing walls, wherein each reinforcing member has two lateral edges deformable by manual application of pressure to said lateral edges, so as to radially distend the outlet opening, wherein the first and second deformable reinforcing members are offset from each other along a longitudinal axis; (c) a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; (d) first and second fasteners; and (e) a pocket; wherein the outlet is flexible and foldable from an open condition to a closed condition by one or more folds, and the outlet in the closed condition is further foldable to be tucked inside the pocket.

A further embodiment provides an ostomy pouch comprising: (a) opposing walls having a cavity therebetween, the walls joined along their peripheries, and tapering to an outlet opening at the proximal end of the device; (b) first and second deformable reinforcing members attached to opposing exterior surfaces of said opposing walls, wherein each reinforcing member has two lateral edges deformable by manual application of pressure to said lateral edges, so as to radially distend the outlet opening, wherein the first and second deformable reinforcing members are offset from each other along a longitudinal axis; (c) a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; (d) first and second fasteners; and (e) a pocket; wherein the outlet is flexible and foldable from an open condition to a closed condition by one or more folds, and the outlet in the closed condition is further foldable to be tucked inside the pocket.

In some embodiments, the medical devices or pouches disclosed herein contain opposing walls having a cavity therebetween, the walls tapering to an outlet having an opening at the distal end; at least one deformable reinforcing member positioned laterally across the tapered end for radially distending and opening the outlet; the outlet being flexible, foldable and securable from an open condition to a closed condition. In some embodiments, the securing means consists of at least two opposable fasteners capable of forming a linkage to seal the device after at least one lateral fold of the outlet. In other embodiments, the securing means may provide structural support for radially distending and opening the outlet. In yet other embodiments, at least one of the opposable fasteners of the securing means consists of a security flap for securing the outlet in a closed position after at least one lateral fold of the outlet.

In certain embodiments, the device claimed is a medical device with an opening system comprising; opposing walls having a cavity therebetween, the walls tapering to an outlet having an opening; first and second deformable reinforcing members attached to opposing exterior surfaces of said opposing walls, wherein each reinforcing member has two lateral edges deformable by manual application of pressure to said lateral edges, so as to radially distend the outlet opening; and the outlet being flexible and foldable from an open condition to a closed condition. In certain embodiments, the medical device with an opening system further comprises a system for securing the device in the closed condition, the system comprising; a first fastener, wherein the first fastener is attached to the same exterior surface of one of said opposing walls as said first reinforcing member, distal to the opening with respect to said first reinforcing member; a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; and a second fastener attached to the freely opened portion of said security flap, wherein the first fastener and the second fastener are capable of forming a linkage when the outlet is in the closed condition. In certain embodiments, at least one of the first and second fasteners is a hook and loop fastener. In certain embodiments, the first deformable reinforcing member is near the outlet opening, and the second deformable reinforcing member is distal to the outlet opening with respect to the first deformable reinforcing member. In certain embodiments, the second deformable reinforcing member is near the outlet opening, and the first deformable reinforcing member is distal to the outlet opening with respect to the second deformable reinforcing member. In certain embodiments, the first and second deformable reinforcing members differ in size. In certain embodiments, the first and second deformable reinforcing members differ in shape. In certain embodiments, the horizontal and/or vertical centerlines of the first and second deformable reinforcing members are offset relative to each other. In certain embodiments, the lateral edges of the first and second reinforcing members have material removed to create corners with void space. In certain embodiments, at least one of the first and second deformable reinforcing members extend the entire width of the outlet opening. In certain embodiments, at least one of the first and second fasteners extend the entire width of the outlet opening. In certain embodiments, the first and second fasteners differ in size. In certain embodiments, the first and second fasteners differ in shape. In certain embodiments, the first and second fastener form a linkage after two lateral folds of the outlet.

In certain other embodiments, the device claimed is a medical device with an opening system comprising; opposing walls having a cavity therebetween, the walls tapering to an outlet having an opening; a deformable reinforcing member on one exterior surface of said opposing walls, near the outlet, said reinforcing member having two lateral edges deformable by manual application of pressure to said lateral edges, so as to radially distend the outlet opening; a first fastener and a second fastener attached to opposing exterior surfaces of said opposing walls, wherein one of said first and second fastener is near the outlet opening; the outlet being flexible and foldable from an opened condition to a closed condition, and wherein the first and second fastener are capable of forming a linkage when said outlet is in the closed condition. In certain other embodiments the device further comprises a system for securing the device in the closed condition, the system comprising; a security flap, wherein said flap is attached to one exterior surface of said opposing walls, distal to the opening of the outlet with respect to said deformable reinforcing member, wherein a portion of the flap extends freely from said one exterior surface of said opposing wall to which the flap is attached; a third fastener attached to one exterior surface of said opposing pouch walls, and a fourth fastener attached to the freely opened portion of the security flap, wherein said third and fourth fastener can form a linkage when said outlet is in the closed condition. In certain embodiments, at least one of the first, second, third and fourth fasteners is a hook and loop fastener. In certain embodiments, the first fastener is attached to the deformable reinforcing member having two lateral edges and is deformable by manual application of pressure to said lateral edges, so as to controllably distend the outlet opening. In certain embodiments, the second fastener is attached to the deformable reinforcing member having two lateral edges, and is deformable by manual application of pressure to said lateral edges, so as to controllably distend the outlet opening. In certain embodiments, the lateral edges of the deformable reinforcing member have material removed to create corners with void space. In certain embodiments, at least one of the first, second, third, and fourth fasteners differs in shape with respect to any other fastener. In certain embodiments, at least one of the first, second, third, and fourth fasteners differs in size with respect to any other fastener. In certain embodiments, the first and second fasteners form a linkage after two lateral folds of the outlet. In certain embodiments, the third and fourth fasteners form a linkage after two lateral folds of the outlet.

In certain embodiments, the medical device claimed is a ostomy pouch with an opening system comprising; opposing walls having a cavity therebetween, the walls tapering to an outlet having an opening; first and second deformable reinforcing members attached to opposing exterior surfaces of said opposing walls, wherein each reinforcing member has two lateral edges deformable by manual application of pressure to said lateral edges, so as to radially distend the outlet opening; and the outlet being flexible and foldable from an open condition to a closed condition. In certain embodiments, the ostomy pouch with an opening system further comprises a system for securing the ostomy pouch in the closed condition, the system comprising; a first fastener, wherein the first fastener is attached to the same exterior surface of one of said opposing walls as said first reinforcing member, distal to the opening with respect to said first reinforcing member; a security flap, wherein said flap is attached to the same exterior surface of one of said opposing walls as the second reinforcing member, distal to the opening of the outlet with respect to the second reinforcing member, wherein a portion of the flap extends freely from the exterior surface of the opposing wall on which the flap is attached; and a second fastener attached to the freely opened portion of said security flap, wherein the first fastener and the second fastener are capable of forming a linkage when the outlet is in the closed condition. In certain embodiments, at least one of the first and second fasteners is a hook and loop fastener. In certain embodiments, the first deformable reinforcing member is near the outlet opening, and the second deformable reinforcing member is distal to the outlet opening with respect to the first deformable reinforcing member. In certain embodiments, the second deformable reinforcing member is near the outlet opening, and the first deformable reinforcing member is distal to the outlet opening with respect to the second deformable reinforcing member. In certain embodiments, the first and second deformable reinforcing members differ in size. In certain embodiments, the first and second deformable reinforcing members differ in shape. In certain embodiments, the horizontal and/or vertical centerlines of the first and second deformable reinforcing members are offset relative to each other. In certain embodiments, the lateral edges of the first and second reinforcing members have material removed to create corners with void space. In certain embodiments, at least one of the first and second deformable reinforcing members extends the entire width of the outlet opening. In certain embodiments, at least one of the first and second fasteners extends the entire width of the outlet opening. In certain embodiments, the first and second fasteners differ in size. In certain embodiments, the first and second fasteners differ in shape. In certain embodiments, the first and second fasteners form a linkage after two lateral folds of the outlet.

In certain other embodiments, the medical device claimed is a ostomy pouch with an opening system comprising; opposing walls having a cavity therebetween, the walls tapering to an outlet having an opening; a deformable reinforcing member on one exterior surface of said opposing walls, near the outlet, said reinforcing member having two lateral edges deformable by manual application of pressure to said lateral edges, so as to radially distend the outlet opening; a first fastener and a second fastener attached to opposing exterior surfaces of said opposing walls, wherein one of said first and second fastener is near the outlet opening; the outlet being flexible and foldable from an opened condition to a closed condition, and wherein the first and second fastener are capable of forming a linkage when said outlet is in the closed condition. In certain other embodiments the ostomy pouch further comprises a system for securing the ostomy pouch in the closed condition, the system comprising; a security flap, wherein said flap is attached to one exterior surface of said opposing walls, distal to the opening of the outlet with respect to said deformable reinforcing member, wherein a portion of the flap extends freely from said one exterior surface of said opposing wall to which the flap is attached; a third fastener attached to one exterior surface of said opposing pouch walls, and a fourth fastener attached to the freely opened portion of the security flap, wherein said third and fourth fastener can form a linkage when said outlet is in the closed condition. In certain embodiments, at least one of the first, second, third and fourth fasteners is a hook and loop fastener. In certain embodiments, the first fastener is attached to the deformable reinforcing member having two lateral edges and is deformable by manual application of pressure to said lateral edges, so as to controllably distend the outlet opening. In certain embodiments, the second fastener is attached to the deformable reinforcing member having two lateral edges, and is deformable by manual application of pressure to said lateral edges, so as to controllably distend the outlet opening. In certain embodiments, the lateral edges of the deformable reinforcing member have material removed to create corners with void space. In certain embodiments, at least one of the first, second, third, and fourth fasteners differs in shape with respect to any other fastener. In certain embodiments, at least one of the first, second, third, and fourth fasteners differs in size with respect to any other fastener. In certain embodiments, the first and second fasteners form a linkage after two lateral folds of the outlet. In certain embodiments, the third and fourth fasteners form a linkage after two lateral folds of the outlet.

BRIEF DESCRIPTION OF THE DRAWINGS

FIG. 18 shows an embodiment of the ostomy pouch where the first and second reinforcing members are offset from each other along a longitudinal axis extending between the proximal end and the distal end of the ostomy pouch.

DETAILED DESCRIPTION OF THE INVENTION

The present disclosure is directed to medical devices, such as an ostomy pouch, which enables easy and reliable drainage of bodily waste from stoma of a patient. In some embodiments, the medical device comprises an ostomy pouch with two opposing walls tapering to an outlet opening such that the pouch may be configured to a closed condition by folding of the outlet and to an open condition by unfolding of the outlet. The shape, size, and position of the various elements included in the medical device, as described below in detail, provide improved closure of the ostomy pouch as well as easy opening/closing of the outlet without requiring difficult manipulation. Thus, the present disclosure includes features that allow a user, even with limited dexterity, to easily manipulate the pouch from an open to a closed condition and vice versa.

Embodiments of the invention are now described with reference to the accompanying drawings.

Figure 1:
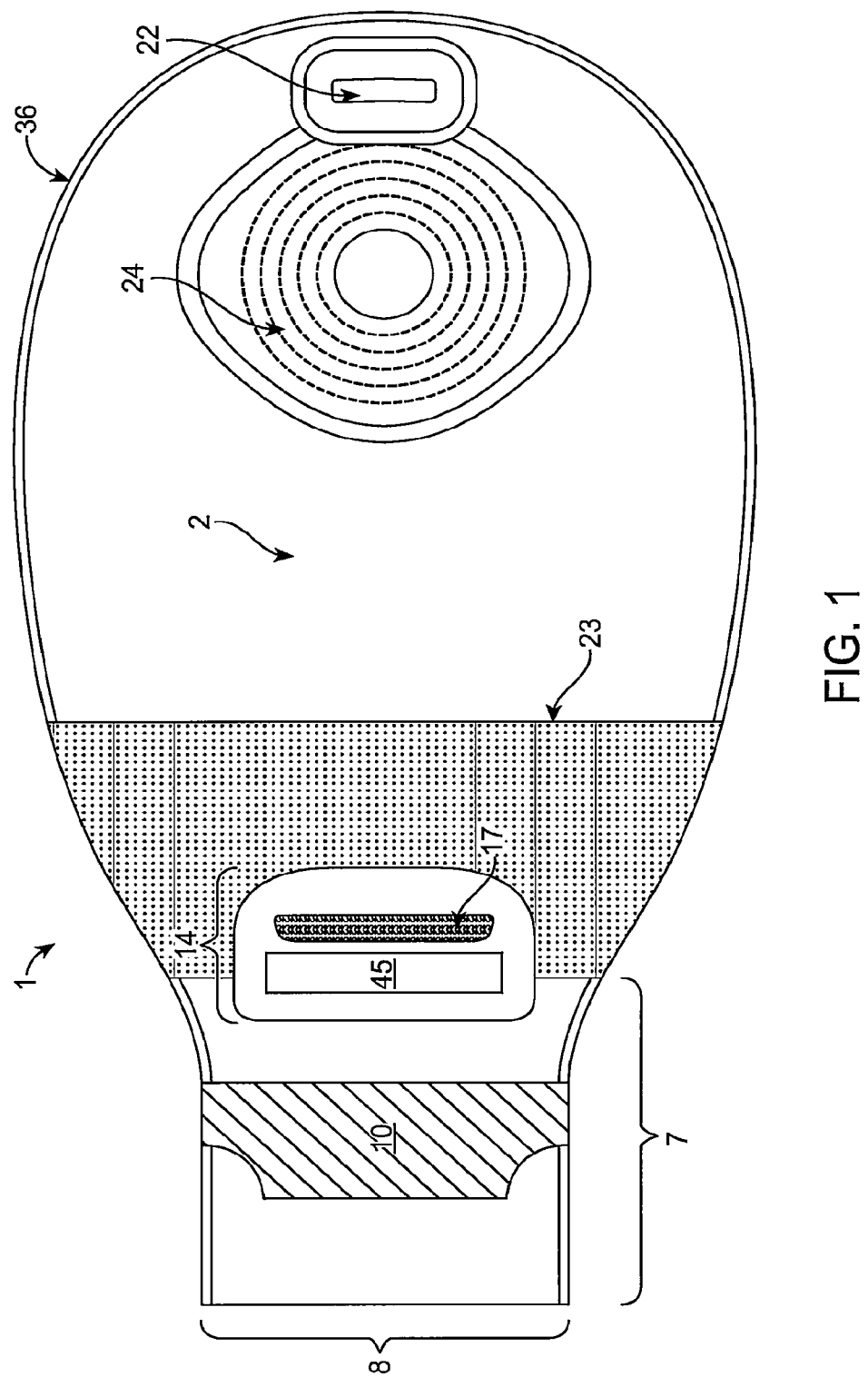
FIG. 1 shows a schematic front view of an embodiment of an ostomy pouch with opening system.
Figure 2:
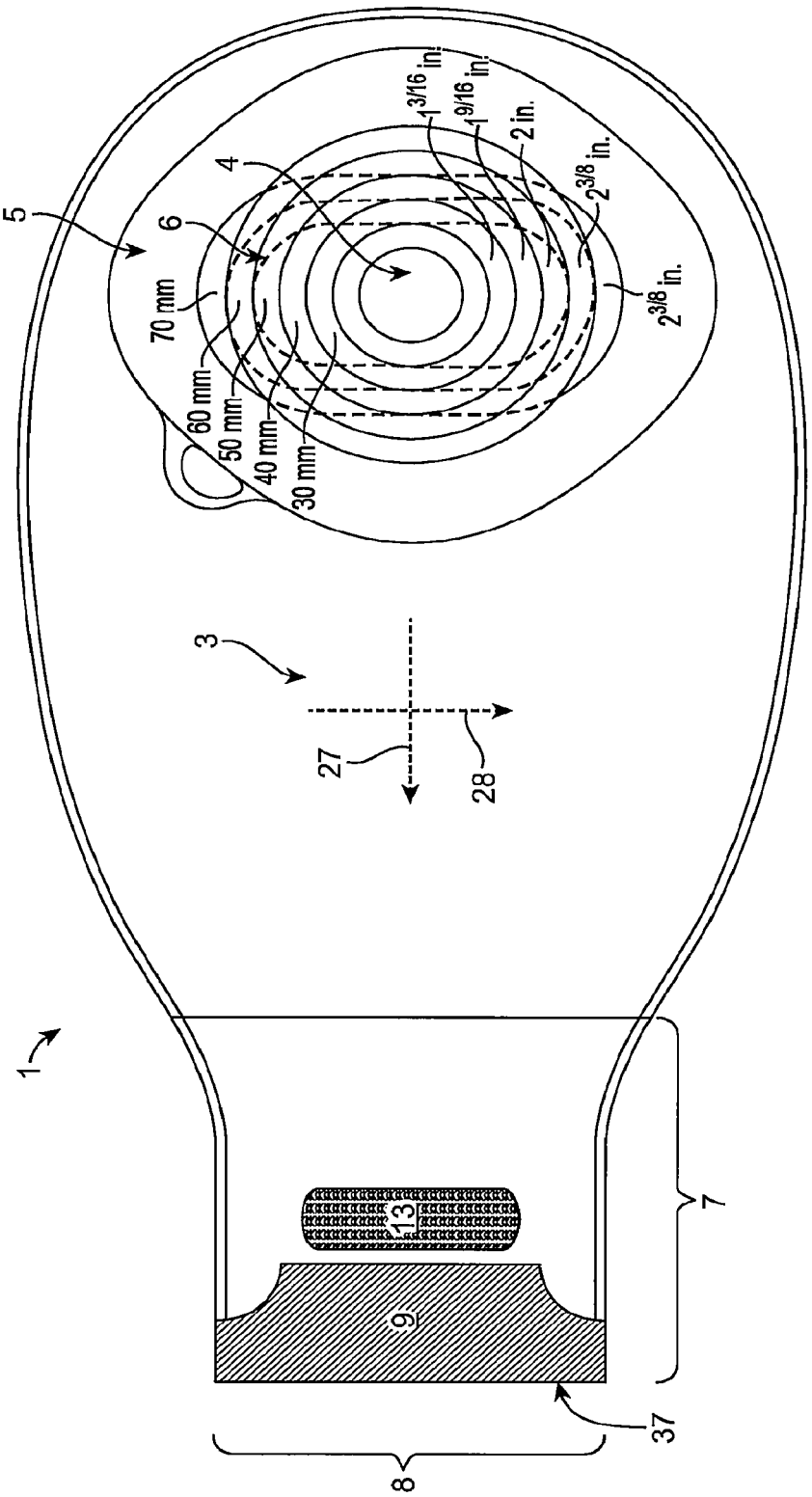
FIG. 2 shows a schematic rear view of an embodiment of the ostomy pouch with opening system.

Referring to FIGS. 1 and 2, the medical device or pouch 1 is formed from a front wall 2 and a rear wall 3. In use, the front wall of the medical device generally faces away from the body, while the rear wall of the medical device or pouch generally faces towards the body. The front and rear wall may comprise at least two separate pieces of material joined together at the edges by adhesive or welding, or may be a single contiguous piece of material. The walls may be constructed of a suitable moisture impermeable material. The walls may be made of transparent or translucent material.

The transparent or translucent walls may further comprise at least one flap that partially or fully covers the front wall. The flap can be manipulated to view the contents of the medical device or pouch and/or to assist a user or patient in attaching the device. In certain embodiments, the flap is opened or closed by a user or patient to view the contents of the medical device or pouch, or to assist in manipulation of the device or pouch onto, for example, the stoma of a patient. In some embodiments, the flap material consists of the same water impermeable material as the front and rear walls. In other embodiments, the flap material consists of a soft, breathable fabric that reduces irritation or chafing to the skin of a patient. The flap material may further be secured in a closed position to mask the contents within the pouch or medical device In some embodiments, the front wall is made of transparent or translucent material and the rear wall is made of opaque material. In other embodiments, the front and rear wall may be made of opaque material. In other embodiments, the walls may be made of opaque material with a transparent window 24 for monitoring the contents of the medical device or pouch, or to assist in attaching the medical device or pouch directly or indirectly onto the patient. The transparent window may further comprise a flap that can be opened and closed to view the contents of the device and/or to assist the user or patient in attachment of the medical device or pouch. The material comprising the front and rear walls as well as the flap may be a plastic, thermoplastic, polymer or a natural substance. The material may be a laminate consisting of a plurality of layers or a single layer. Suitable materials include but are not limited to ethylene vinyl acetate (EVA), polyvinylidene chloride (PVDC), or ethylene vinyl alcohol (EVOH). In certain embodiments, the front and rear wall material further comprises an anti-microbial substance or coating, or the material itself has anti-microbial properties. Exemplary materials for a coating include, but are not limited to, metals or metal alloys of silver, gold, gallium, titanium, titanium dioxide or copper; organosilanes; and quaternary ammonium compounds such as 3-(Trimethoxysilyl)-propyldimethyloctadecyl ammonium chloride (Si-QAC).

In certain embodiments, the front and rear wall material for the construction of the device walls provides controls for unpleasant odor. In further embodiments, the medical device or pouch further comprises a deodorizing filter and vent 22 for deodorizing and venting flatus. In some embodiments, the filter is a strip filter or an axial filter. In other embodiments, the strip filter or axial flow filter is wrapped with an odor barrier film around its perimeter. In yet other embodiments, the filter has a low profile. In still other embodiments, an open cell foam is added as a pre-filter to prevent solid components from entering into and fouling the filter. In certain embodiments, the filter contains activated carbon.

In some embodiments, the medical device or pouch includes a first comfort layer covering at least part of the rear wall 3 and a second comfort layer covering at least part of the front wall 2. In some embodiments, wherein the front wall 2 is made of a transparent material a comfort layer does not cover the front wall 2. In some embodiments, wherein the rear wall 3 is made of an opaque material, it is covered, at least partially, by a comfort layer. In some embodiments, the comfort layer is partially sealed to the front or rear wall that it covers so as to leave an access opening between the comfort layer(s) and the wall it is covering. In some embodiments, the access opening is perpendicular to the longitudinal axis 27 of the medical device or pouch and proximate to where the walls taper to the outlet 7. Exemplary materials for the comfort layer include, but are not limited to, film, foam, woven or non-woven fabric.

Figure 16:
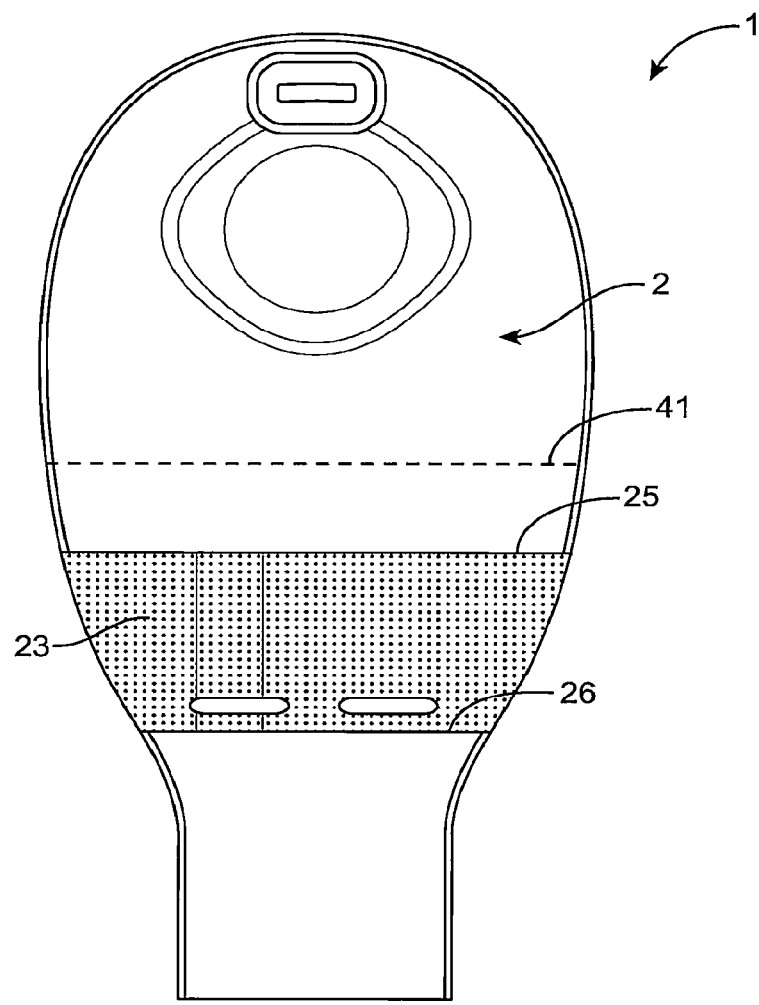
FIG. 16 shows a schematic front view of an embodiment of the ostomy pouch containing a pocket.
Figure 17:
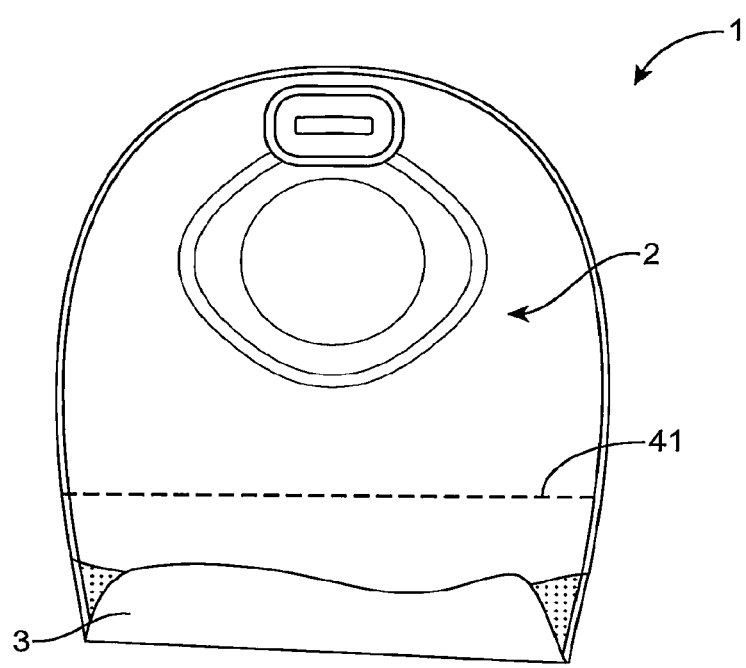
FIG. 17 shows a schematic front view of an embodiment of the ostomy pouch containing a pocket and folded and tucked inside the pocket.

In certain embodiments, the device contains a pocket 23 (FIG. 16). In certain embodiments, the outlet 7, in the closed condition, can be further folded and tucked into pocket 23 to allow for further security in the closure. In certain embodiments, the pocket 23 is attached to the front wall 2 of the device. In some embodiments, the pocket 23 is attached to front wall 2 along the periphery of the pouch and has a top edge 25 and a bottom edge 26. In some embodiments, the top edge 25 of pocket 23 is positioned below the horizontal centerline 41 of pouch 1. In some embodiments, the top edge 25 of pocket 23 is positioned at the horizontal centerline 41 of pouch 1. In some embodiments, the top edge 25 of pocket 23 is positioned above the horizontal centerline 41 of pouch 1. In some embodiments, pocket 23 is made of the same material as that of at least one of the walls. In some embodiments, pocket 23 is made of a different material than that of the walls. Exemplary materials for the pocket include, but are not limited to, film, foam, woven or non-woven fabric.

The rear wall 3 of the medical device or pouch (FIG. 2) contains an opening comprising a stomal aperture 4 to allow connection to a stoma or peristomal area. The stomal aperture further connects to an adhesive wafer or gasket 5, which is attached to or around the stoma or peristomal area. The adhesive wafer contains a skin compatible adhesive or sealant for attaching the device to the peristomal skin. In some embodiments, the adhesive or sealant is moldable. In certain embodiments, the adhesive wafer is removable from the device so that it might be positioned by the user around a stoma before the medical device or pouch is attached. In other embodiments, the adhesive wafer is attached to the medical device or pouch. In some embodiments, the adhesive wafer 5 and/or stomal aperture 4 further comprise exemplary marks or indications 6 that allow the user to adjust the size of the aperture. In further embodiments, the rear wall 3 may additionally comprise a coating or additional layer of material to enhance the comfort or breathability of the medical device or pouch when worn by a patient.

Figure 7:
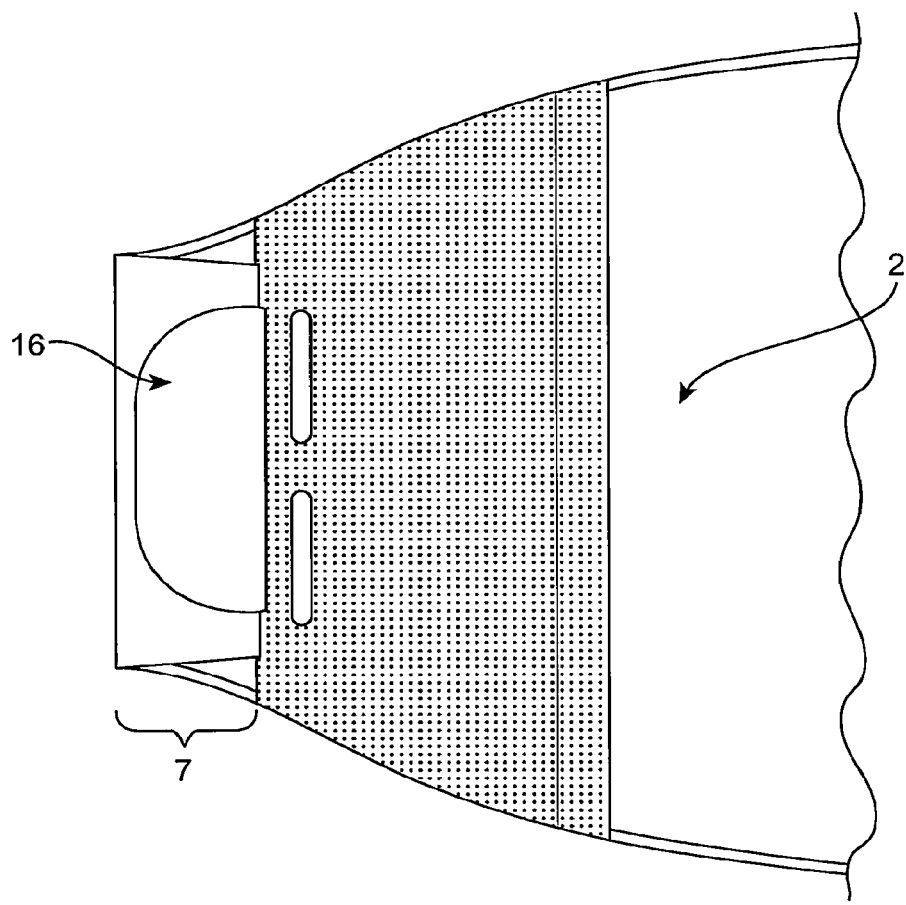
FIG. 7 shows a schematic front view of an embodiment of the ostomy pouch with detail of the outlet in a closed condition.
Figure 9:
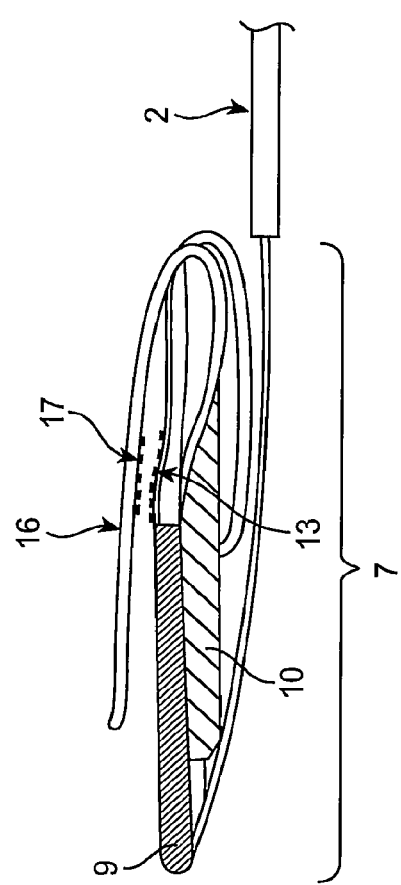
FIG. 9 shows a schematic side view of an embodiment of the ostomy pouch with detail of the first and second fasteners forming a linkage when the outlet is in a closed condition.

The medical device or pouch further tapers to an outlet 7 (FIGS. 1 and 2) with an outlet opening 8. In some embodiments, the outlet opening 8 may be at the proximal end of the device. In some embodiments, the outlet opening 8 may extend the entire width of the outlet. In some embodiments, the opening may extend only partially the width of the outlet. In some embodiments, the outlet is foldable from an open (FIGS. 3 and 4) to a closed condition (FIGS. 7 and 9). In certain embodiments, the outlet requires a single lateral fold. In some embodiments, the outlet requires at least two lateral folds to be in a closed condition. In certain embodiments, the outlet requires two lateral folds to be in a closed condition. In certain embodiments, the outlet requires three lateral folds to be in a closed condition. In certain embodiments, the outlet requires four lateral folds to be in a closed condition. In certain embodiments, the outlet requires five lateral folds to be in a closed condition. In some embodiments, the lateral fold results in folding of the outlet in an upward direction away from the opening. In some embodiments, the first reinforcing member is positioned above the second reinforcing member by a single lateral fold of the outlet. In some embodiments, the first reinforcing member is stacked on top of the second reinforcing member and the first fastener is stacked on top of the first reinforcing member by two lateral folds of the outlet. In some embodiments, the first fastener forms a linkage with the second fastener by three lateral folds of the outlet.

Different embodiments of the opening system for the medical device will now be described.

Figure 3:
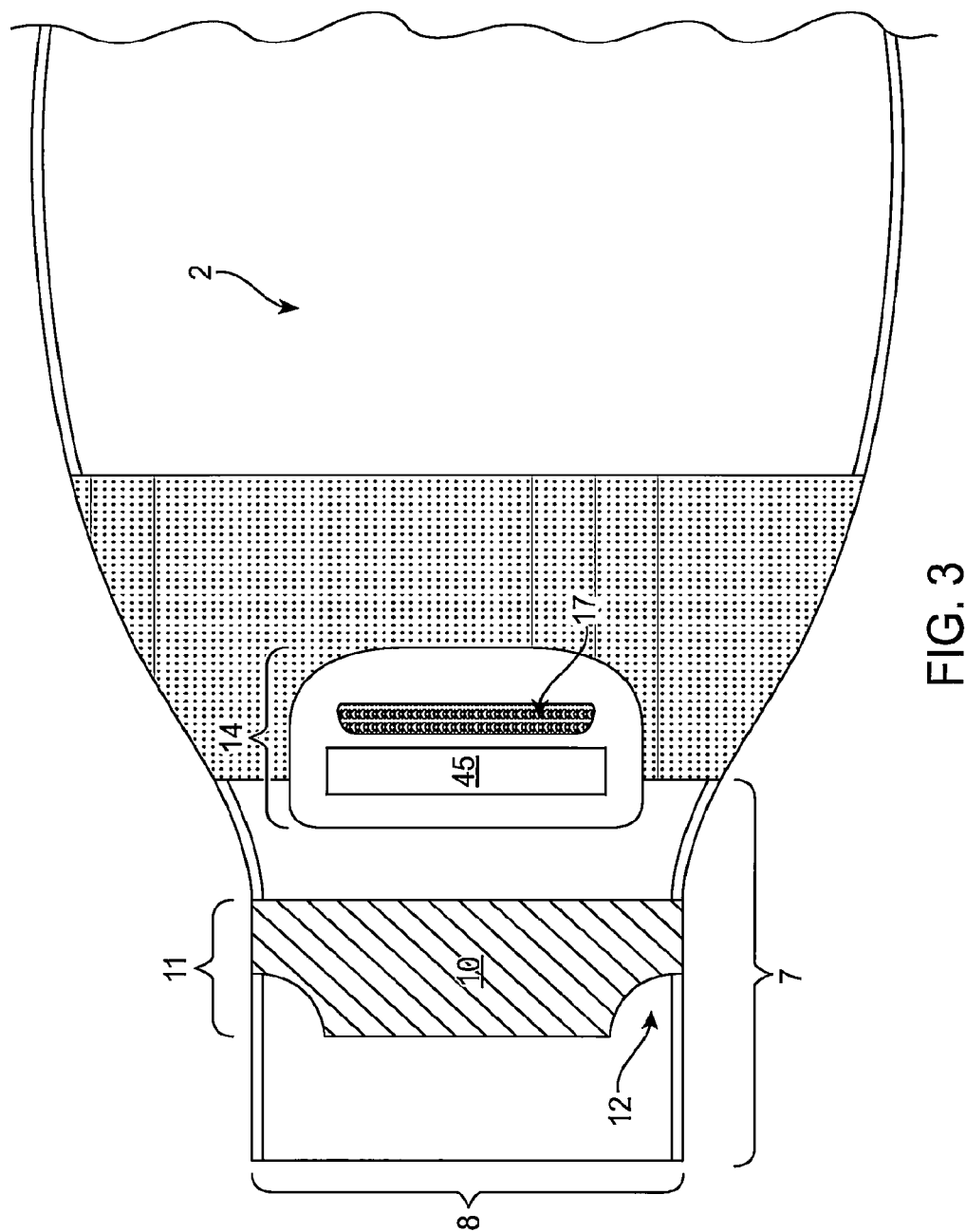
FIG. 3 shows a schematic front view of an embodiment of the ostomy pouch with detail of the outlet in an open condition.
Figure 4:
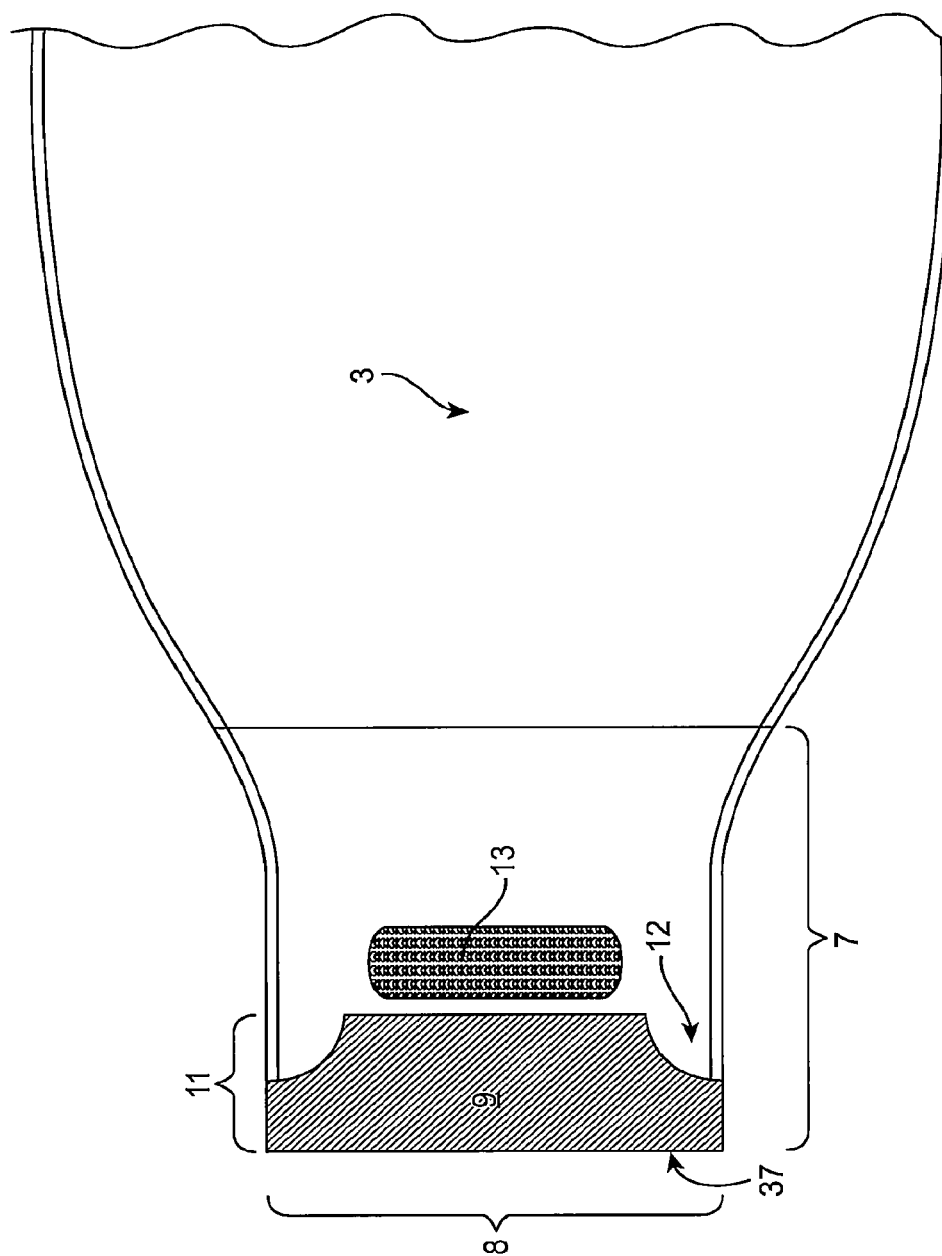
FIG. 4 shows a schematic rear view of an embodiment of the ostomy pouch with detail of the outlet in an open condition.
Figure 8:
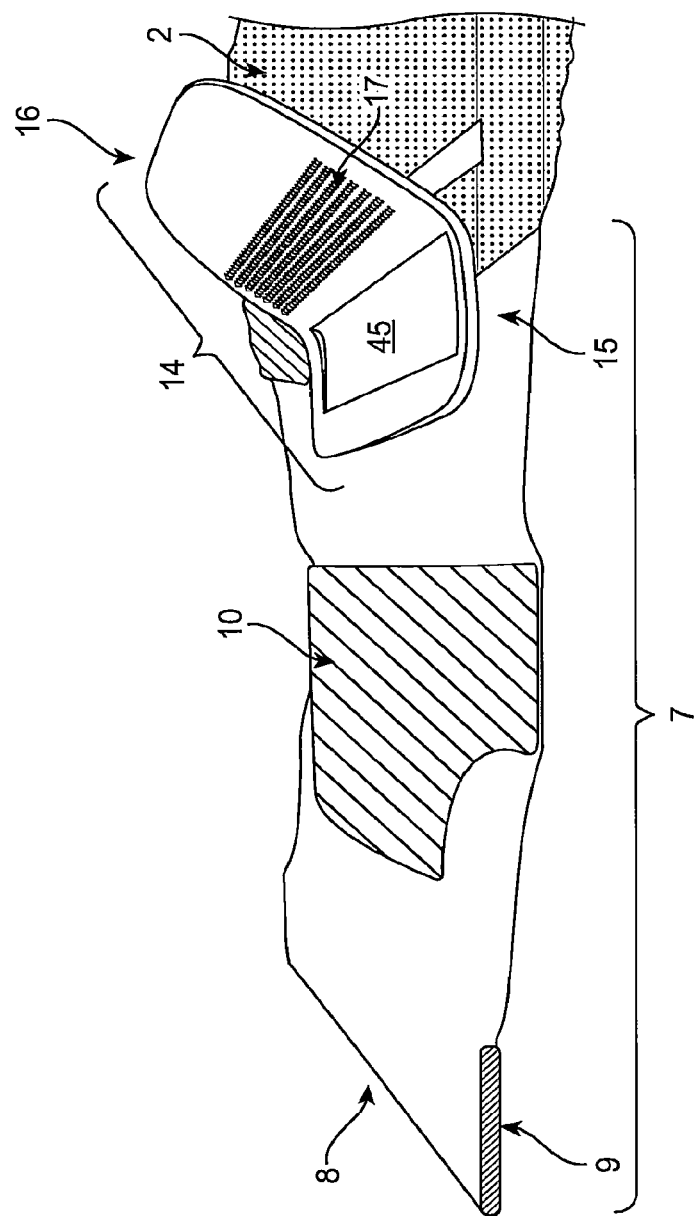
FIG. 8 shows a schematic side view of an embodiment of the ostomy pouch with detail of the attachment of the security flap to the outlet, when the outlet is in an open condition.

Referring to the first embodiment of the medical device with an opening system, as illustrated in FIGS. 3, 4 and 8, the outlet has an opening system with at least a first reinforcing member 9 (FIG. 4) and a second (FIG. 3) reinforcing member 10, each of which is attached to an exterior surface of the device on the outlet 7.

In some embodiments, the first reinforcing member and the second reinforcing member are made of the same material. In some embodiments, the first reinforcing member and the second reinforcing member are made of different materials. In some embodiments, the first reinforcing member and the second reinforcing member are each independently made of a resiliently flexible, easily distensible plastic material. In some embodiments, the resiliently flexible easily distensible plastic material is not compressible. Non-limiting examples of resiliently flexible, easily distensible plastic material include polystyrene, polyethylene, polyurethane, polyester, polycarbonate. In preferred embodiments, the first and second reinforcing members are each made of polystyrene. In some embodiments, the first reinforcing member and the second reinforcing member are each independently made of a resiliently flexible metal sheet.

Figure 18B:
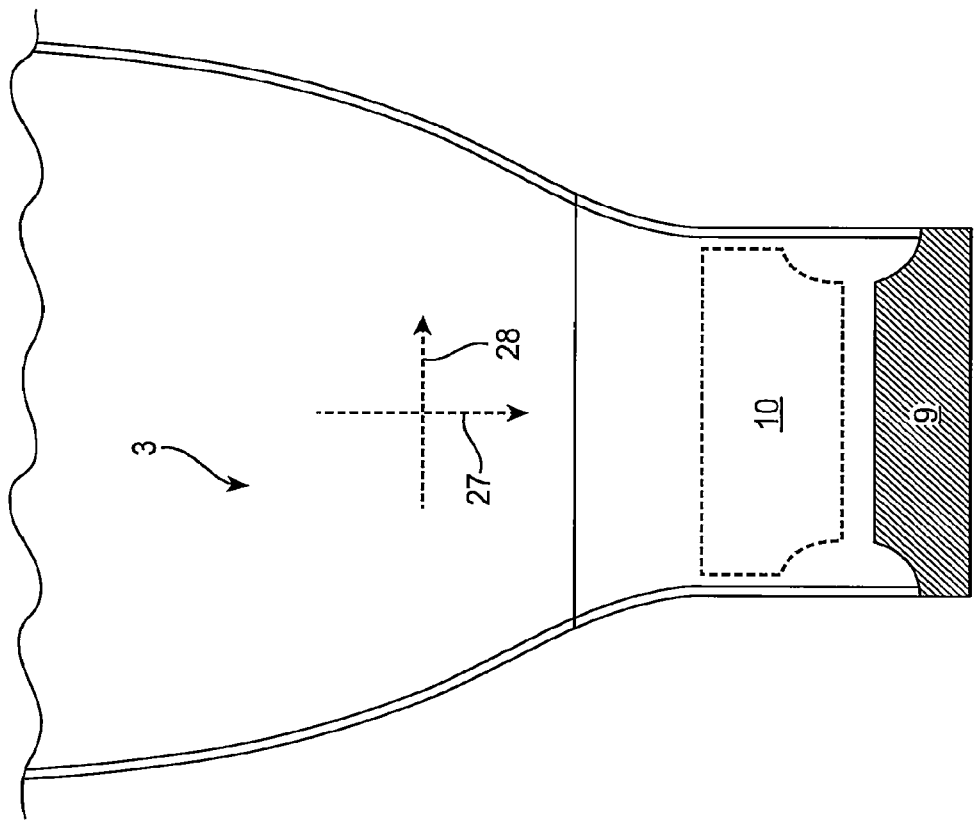
FIG. 18A shows a front view of the ostomy pouch and FIG. 18B shows a rear view of the ostomy pouch.
Figure 18A:
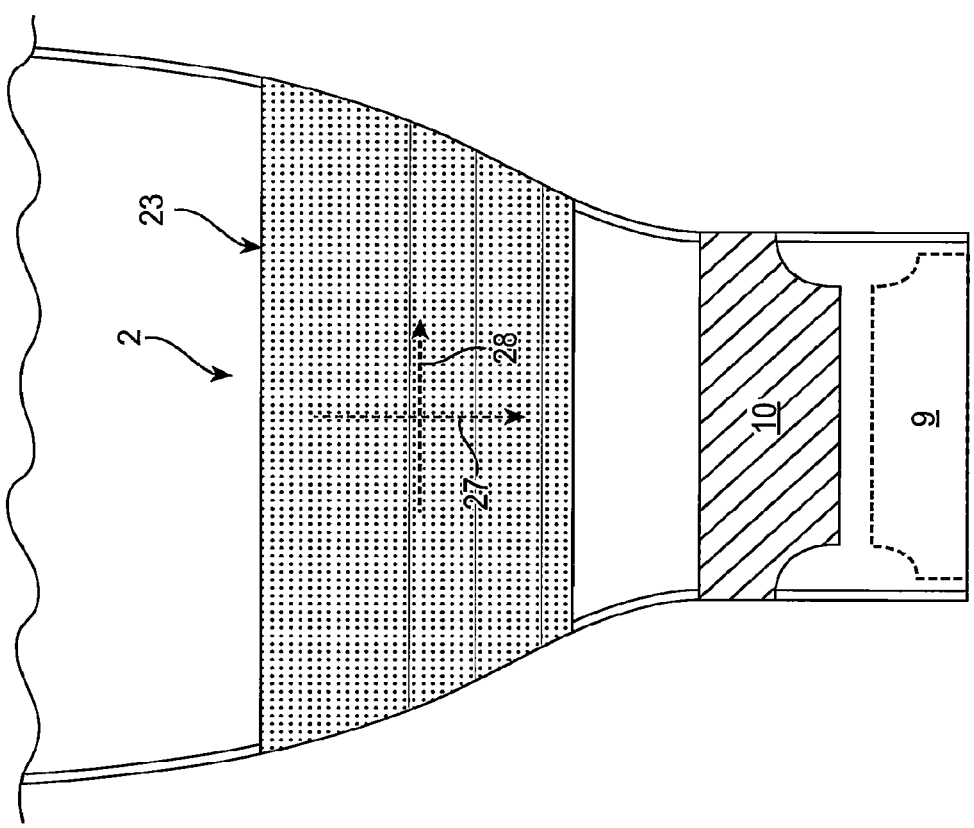

The first and second reinforcing members may be attached to opposing exterior surfaces on the walls. The horizontal centerlines of the first and second reinforcing members may be offset with respect to each other as shown in FIGS. 8 and 18. In some embodiments, the offset of the first and second reinforcing members may enable easy folding and handling of the medical device, for draining and closing. For example, users with poor dexterity may also benefit from the easy folding allowed by the offset of the first and second reinforcing members. The first and second reinforcing members may be vertically offset relative to each other, i.e., the vertical centerlines of the first and second reinforcing members may be offset relative to each other. In some embodiments, the vertical centerline may be a line running along the axis 27 which extends from the proximal end to the distal end of the device. In some embodiments, the horizontal centerline may be a line running along the axis 28 which runs perpendicular to the axis 27. The horizontal and vertical centerlines of the first and second reinforcing members may be offset relative to each other. The horizontal centerlines of the first and second reinforcing members may be offset relative to each other by about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 mm or more. The vertical centerlines of the first and second reinforcing members may preferably be offset relative to each other by about 0, 1, 2, 3, 4, 5, 6, 7, 8, 9 or 10 mm or more. More preferably, the horizontal and/or vertical centerlines of the first and second reinforcing members may be offset relative to each other by about 0, 1, 2, 3, 4, 5, 6, 7, 8, 9, 10 mm or more. Most preferably, the horizontal and/or vertical centerlines of the first and second reinforcing members may be offset relative to each other by about 0, 1, 2, 3, 4, 5 mm or more. In some embodiments, the horizontal centerlines of the first and second reinforcing members are offset relative to each other by about 1-5 mm. In some embodiments, the horizontal centerlines of the first and second reinforcing members are offset relative to each other by about 1-10 mm. In some embodiments, the horizontal centerlines of the first and second reinforcing members are offset relative to each other by about 1-20 mm. In some embodiments, the horizontal centerlines of the first and second reinforcing members are offset relative to each other by about 1-30 mm. In some embodiments, the horizontal centerlines of the first and second reinforcing members are offset relative to each other by about 5-10 mm. In some embodiments, the horizontal centerlines of the first and second reinforcing members are offset relative to each other by about 5-20 mm. In some embodiments, the horizontal centerlines of the first and second reinforcing members are offset relative to each other by about 5-30 mm. In some embodiments, the horizontal centerlines of the first and second reinforcing members are offset relative to each other by about 10-20 mm. In some embodiments, the horizontal centerlines of the first and second reinforcing members are offset relative to each other by about 10-30 mm. In some embodiments, the horizontal centerlines of the first and second reinforcing members are offset relative to each other by about 20-30 mm. The horizontal centerlines of the first and second reinforcing members may not be offset with respect to each other, but positioned at equal distances from the edge of the outlet opening.

In some embodiments, the first and second reinforcing members may be offset relative to each other, along a longitudinal axis by about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 mm or more. In some embodiments, the first and second reinforcing members may be offset relative to each other, along a longitudinal axis by about 1-5 mm. In some embodiments, the first and second reinforcing members may be offset relative to each other, along a longitudinal axis by about 1-10 mm. In some embodiments, the first and second reinforcing members may be offset relative to each other, along a longitudinal axis by about 1-20 mm. In some embodiments, the first and second reinforcing members may be offset relative to each other, along a longitudinal axis by about 1-30 mm. In some embodiments, the first and second reinforcing members may be offset relative to each other, along a longitudinal axis by about 5-10 mm. In some embodiments, the first and second reinforcing members may be offset relative to each other, along a longitudinal axis by about 5-20 mm. In some embodiments, the first and second reinforcing members may be offset relative to each other, along a longitudinal axis by about 5-30 mm. In some embodiments, the first and second reinforcing members may be offset relative to each other, along a longitudinal axis by about 10-20 mm. In some embodiments, the first and second reinforcing members may be offset relative to each other, along a longitudinal axis by about 10-30 mm. In some embodiments, the first and second reinforcing members may be offset relative to each other, along a longitudinal axis by about 20-30 mm. In some embodiments, the first and second reinforcing members may not be offset with respect to each other along a longitudinal axis, but positioned at equal distances from the edge of the outlet opening.

In some embodiments, the vertical centerlines of the first and second reinforcing members are offset relative to each other by about 1-5 mm. In some embodiments, the vertical centerlines of the first and second reinforcing members are offset relative to each other by about 1-10 mm. In some embodiments, the vertical centerlines of the first and second reinforcing members are offset relative to each other by about 1-20 mm. In some embodiments, the vertical centerlines of the first and second reinforcing members are offset relative to each other by about 1-30 mm. In some embodiments, the vertical centerlines of the first and second reinforcing members are offset relative to each other by about 5-10 mm. In some embodiments, the vertical centerlines of the first and second reinforcing members are offset relative to each other by about 5-20 mm. In some embodiments, the vertical centerlines of the first and second reinforcing members are offset relative to each other by about 5-30 mm. In some embodiments, the vertical centerlines of the first and second reinforcing members are offset relative to each other by about 10-20 mm. In some embodiments, the vertical centerlines of the first and second reinforcing members are offset relative to each other by about 10-30 mm. In some embodiments, the vertical centerlines of the first and second reinforcing members are offset relative to each other by about 20-30 mm.

In a first embodiment of the medical device with an opening system, shown in FIG. 8, a second reinforcing member 10 is distal to the opening 8 with respect to the first reinforcing member 9. In the first embodiment of the medical device with an opening system, shown in FIG. 4, the first reinforcing member 9 is immediately adjacent to the opening or its bottom edge 37 is offset from the opening by about 1, 2, 3, 4, 5, 6, 7, 8, 9, 10, 11, 12, 13, 14, 15, 16, 17, 18, 19, 20 mm or more. In some embodiments, the bottom edge 37 of the first reinforcing member 9 is offset from the opening by about 1 mm. In some embodiments, the bottom edge 37 of the first reinforcing member 9 is offset from the opening by about 2 mm. In some embodiments, the bottom edge 37 of the first reinforcing member 9 is offset from the opening by about 3 mm. In some embodiments, the bottom edge 37 of the first reinforcing member 9 is offset from the opening by about 4 mm. In some embodiments, the bottom edge 37 of the first reinforcing member 9 is offset from the opening by about 5 mm. In some embodiments, the bottom edge 37 of the first reinforcing member 9 is offset from the opening by about 6 mm. In some embodiments, the bottom edge 37 of the first reinforcing member 9 is offset from the opening by about 7 mm. In some embodiments, the bottom edge 37 of the first reinforcing member 9 is offset from the opening by about 8 mm. In some embodiments, the bottom edge 37 of the first reinforcing member 9 is offset from the opening by about 9 mm. In some embodiments, the bottom edge 37 of the first reinforcing member 9 is offset from the opening by about 10 mm. In some embodiments, the bottom edge 37 of the first reinforcing member 9 is offset from the opening by more than about 10 mm. In some embodiments, the bottom edge 37 of the first reinforcing member 9 is offset from the opening by about 1-5 mm. In some embodiments, the bottom edge 37 of the first reinforcing member 9 is offset from the opening by about 1-10 mm. In some embodiments, the bottom edge 37 of the first reinforcing member 9 is offset from the opening by about 1-15 mm. In some embodiments, the bottom edge 37 of the first reinforcing member 9 is offset from the opening by about 1-20 mm. In some embodiments, the bottom edge 37 of the first reinforcing member 9 is offset from the opening by about 3-10 mm. In some embodiments, the bottom edge 37 of the first reinforcing member 9 is offset from the opening by about 3-15 mm. In some embodiments, the bottom edge 37 of the first reinforcing member 9 is offset from the opening by about 3-20 mm. In some embodiments, the bottom edge 37 of the first reinforcing member 9 is offset from the opening by about 5-10 mm. In some embodiments, the bottom edge 37 of the first reinforcing member 9 is offset from the opening by about 5-15 mm. In some embodiments, the bottom edge 37 of the first reinforcing member 9 is offset from the opening by about 5-20 mm. In some embodiments, the bottom edge 37 of the first reinforcing member 9 is offset from the opening by about 10-15 mm. In some embodiments, the bottom edge 37 of the first reinforcing member 9 is offset from the opening by about 10-20 mm.

In some embodiments, the length of the first reinforcing member 9 extends essentially the entire width of the opening 8. In some embodiments, the length of the second reinforcing member 10 extends essentially the entire width of the opening 8. In some embodiments, lengths of both the first reinforcing member 9 and the second reinforcing member 10 extend essentially the entire width of the opening 8. In some embodiments, the length of the first reinforcing member 9 extends essentially across the entire width of the opening 8 and the length of the second reinforcing member 10 extends essentially only partially across the width of the opening 8. In preferred embodiments, the length of the first reinforcing member 9 extends essentially the entire width of the opening 8. In preferred embodiments, the length of the second reinforcing member 10 extends essentially only partially across the width of the opening 8.

In some embodiments, both the first reinforcing member 9 and the second reinforcing member 10 are about of the same length. In some embodiments, the first reinforcing member 9 is about 5, 10, 15, 20, 25, 30, 35, 40, 45, 50, 55 mm, 60 mm, 65 mm, 70 mm, 75 mm, 80 mm, 85 mm, or any increment thereof, long. In some embodiments, the first reinforcing member 9 is about 5-85 mm long. In some embodiments, the first reinforcing member 9 is about 5-80 mm long. In some embodiments, the first reinforcing member 9 is about 5-40 mm long. In some embodiments, the first reinforcing member 9 is about 5-70 mm long. In some embodiments, the first reinforcing member 9 is about 5-60 mm long. In some embodiments, the first reinforcing member 9 is about 5-55 mm long. In some embodiments, the first reinforcing member 9 is about 5-50 mm long. In some embodiments, the first reinforcing member 9 is about 5-40 mm long. In some embodiments, the first reinforcing member 9 is about 5-30 mm long. In some embodiments, the first reinforcing member 9 is about 5-20 mm long. In some embodiments, the first reinforcing member 9 is about 5-10 mm long. In some embodiments, the first reinforcing member 9 is about 75-80 mm long.

In some embodiments, the second reinforcing member 10 is about 5, 10, 15, 20, 25, 30, 35, 40, 45, 50, 55 mm, 60 mm, 65 mm, 70 mm, 75 mm, 80 mm, 85 mm, or any increment thereof, long. In some embodiments, the second reinforcing member 10 is about 5-85 mm long. In some embodiments, the second reinforcing member 10 is about 5-80 mm long. In some embodiments, the second reinforcing member 10 is about 5-40 mm long. In some embodiments, the second reinforcing member 10 is about 5-70 mm long. In some embodiments, the second reinforcing member 10 is about 5-60 mm long. In some embodiments, the second reinforcing member 10 is about 5-50 mm long. In some embodiments, the second reinforcing member 10 is about 5-40 mm long. In some embodiments, the second reinforcing member 10 is about 5-40 mm long. In some embodiments, the second reinforcing member 10 is about 5-30 mm long. In some embodiments, the second reinforcing member 9 is about 5-20 mm long. In some embodiments, the second reinforcing member 10 is about 5-10 mm long. In some embodiments, the second reinforcing member 10 is about 75-80 mm long.

In some embodiments, the lengths of the first (9) and second (10) reinforcing members are correlated with preventing incidences of leak from the medical device disclosed herein when it is in a closed condition. For example, the probability of an incidence of leak is about 10% to about 25% less in a medical device where first (9) and second (10) reinforcing members are 80 mm long than in a medical device where the first (9) and second (10) reinforcing members are 50 mm long.

In some embodiments, the first reinforcing member 9 is about 2, 3, 4, 5, 6, 7, 8, 9, 10, 11, 12, 13, 14, 15, 16, 17, 18, 19, or 20 mm wide. In some embodiments, the first reinforcing member 9 is about 2-20 mm wide. In some embodiments, the first reinforcing member 9 is about 5-20 mm wide. In some embodiments, the first reinforcing member 9 is about 10-20 mm wide. In some embodiments, the second reinforcing member 10 is about 2, 3, 4, 5, 6, 7, 8, 9, 10, 11, 12, 13, 14, 15, 16, 17, 18, 19, or 20 mm wide. In some embodiments, the second reinforcing member 10 is about 2-20 mm wide. In some embodiments, the second reinforcing member 10 is about 5-20 mm wide. In some embodiments, the second reinforcing member 10 is about 10-20 mm wide. In some embodiments, the first reinforcing member 9 and the second reinforcing member 10 are offset from each other, along the vertical axis 28, by about 1 mm to about 5 mm. In some embodiments, the widths of the first 9 and second 10 reinforcing members are dependent on the type of material used for the reinforcing members. In some embodiments, the widths of the first 9 and second 10 reinforcing members are proportional to their flexibility. In some embodiments, the first reinforcing member 9 and the second reinforcing member 10 are made of polystyrene and are about 20 mm wide. In some embodiments, the first reinforcing member 9 and the second reinforcing member 10 are made of polyethylene and are about 15 mm wide. In preferred embodiments, the first reinforcing member 9 and the second reinforcing member 10 are made of polystyrene.

Figure 11:
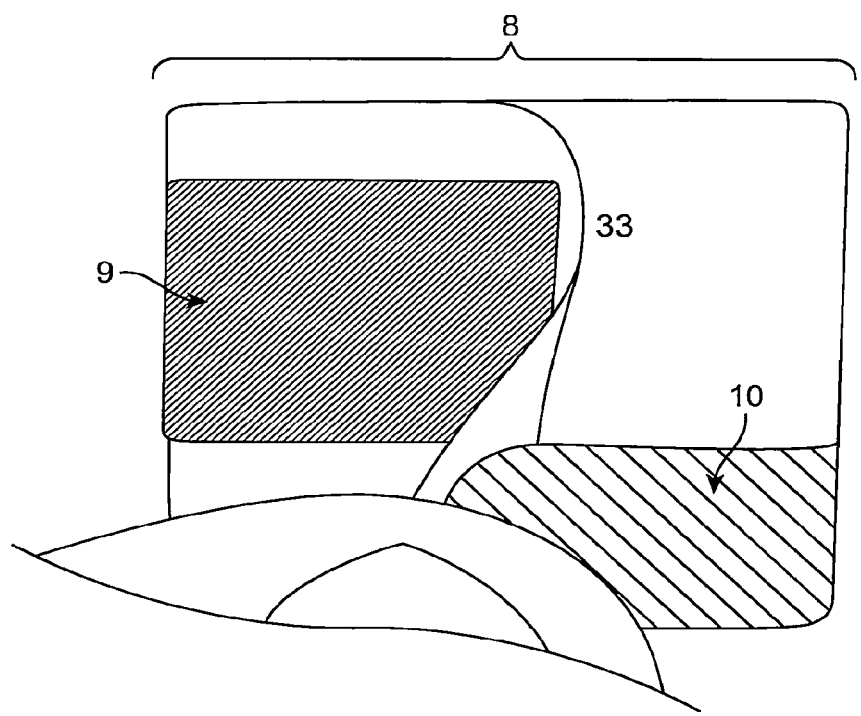
FIG. 11 shows the first and second reinforcing members in a radially distended condition after the manual application of pressure.

Referring to FIGS. 3 and 4, which illustrate a first embodiment of the medical device with an opening system, the first reinforcing member 9 and the second reinforcing member 10 have lateral edges 11. The lateral edges are deformable by application of pressure. FIG. 11 is a side-view of the outlet in use illustrating the application of pressure to the first reinforcing member 9 and the second reinforcing member 10, of the first embodiment, as the opening 8 is radially distended and opened for drainage. A user squeezes together the lateral edges of reinforcing member 9 and reinforcing 10 at the peripheral edge of the outlet 33. While reinforcing member 9 is placed away from edge of the opening 8 in this view, the reinforcing member may be at or near the opening edge 8, for example, at a distance of about 0, 1, 2, 3, 4, 5, 6, 7, 8, 9, 10, 11, 12, 13, 14, 15, 16, 17, 18, 19, 20 mm or more from the opening edge 8. In some embodiments, pressure may be applied to the lateral edges of the first reinforcing member 9 and the second reinforcing member 10 to push the edges from its flat un-deformed state to a curved deformed state inward towards the midline of the opening 8, thereby radially distending the opening 8. Such deformation is reversible when the pressure is removed. The first reinforcing member 9 and the second reinforcing member 10 may have corners that are notched, grooved, cut-to-shape or the like. In some embodiments, the first reinforcing member 9 and the second reinforcing member 10 may have corners that are square, rounded, flared, or have material removed, creating a void 12 (FIGS. 3 and 4) to facilitate finger positioning by a user. The material can be removed from either a single lateral edge or from both lateral edges. In some embodiments, the shape of the first and second reinforcing members may enable easy handling of the medical device, for draining and closing. For example, a user may have his/her fingers fit the notched or voided region of the first and second reinforcing member, to open or close the outlet with ease. Further, users with poor dexterity may also benefit from the notched or voided design of the first and second reinforcing members. The reinforcing member may have corners that are grooved, cut-to-shape or the like to allow finger positioning by a user.

In some embodiments, the first reinforcing member 9 may be positioned above to the second reinforcing member 10 by a single lateral fold of the outlet. In some embodiments, the first reinforcing member 9 may be stacked on top of the second reinforcing member 10 and the first fastener 13 may be stacked on top of the first reinforcing member by two lateral folds of the outlet. In some embodiments, the first fastener 13 may form a linkage with the second fastener 17 by three lateral folds of the outlet, as seen in FIG. 9.

Figure 5:
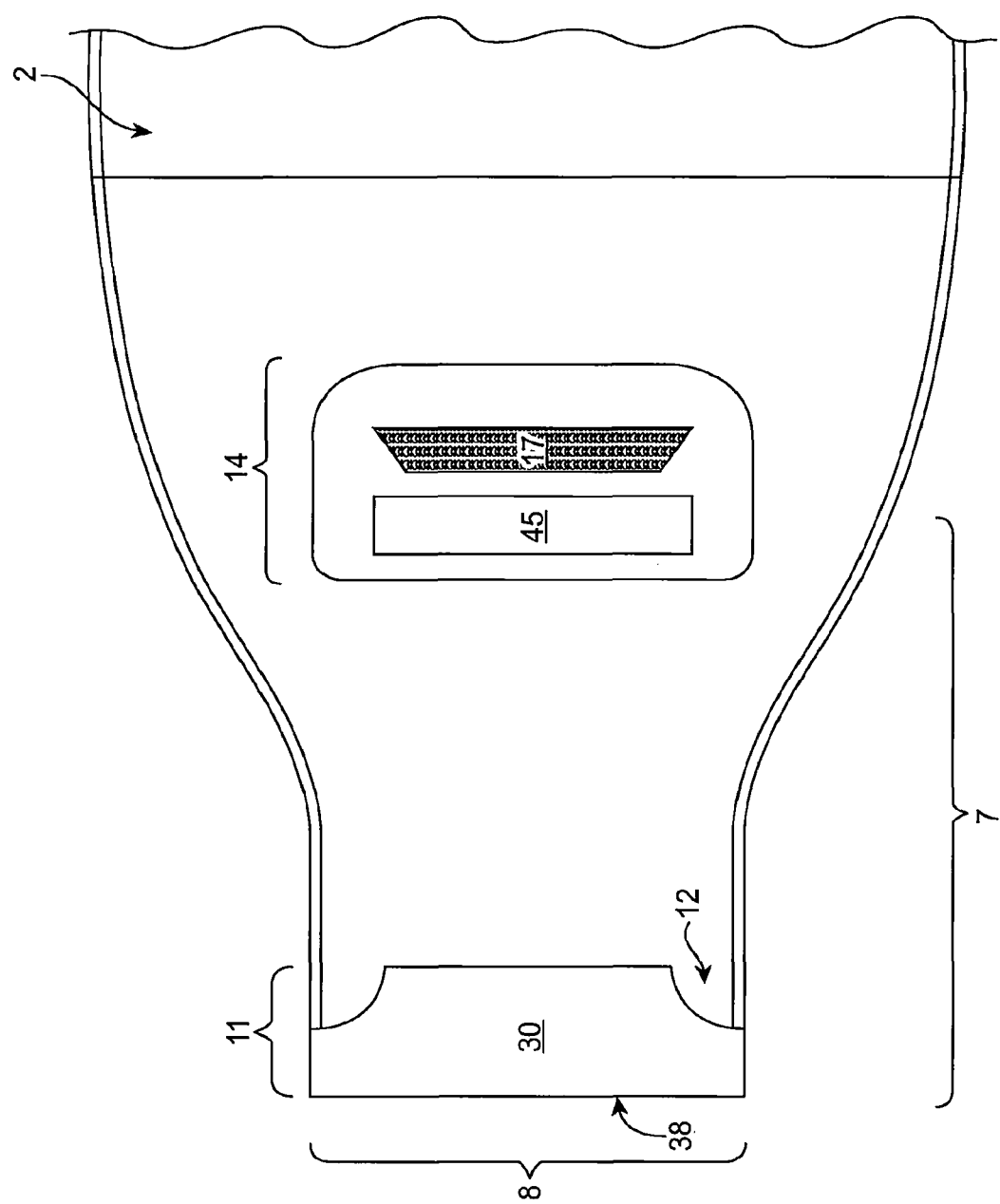
FIG. 5 shows an alternative embodiment of the ostomy pouch with regard to positioning of one of the reinforcing members.
Figure 6:
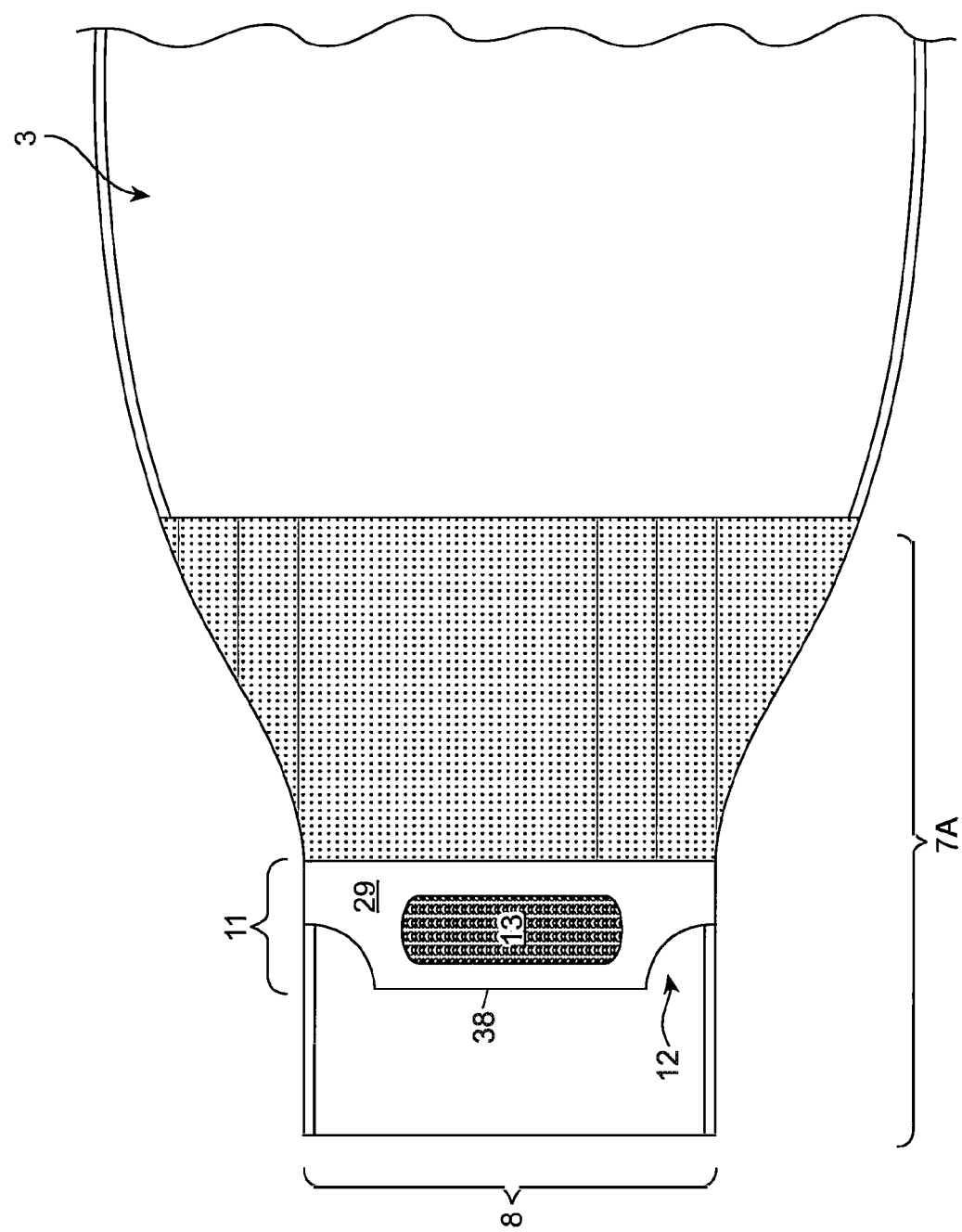
FIG. 6 shows an alternative embodiment of the ostomy pouch, with regard to positioning of one of the reinforcing members and fastener.

In a second embodiment of the medical device with an opening system, as shown in FIGS. 5 and 6, the bottom edge 38 of the first reinforcing member 29 is distal to the opening 8, with respect to the second reinforcing member 30. In the second embodiment of the medical device with an opening system, the bottom edge 38 of the second reinforcing member 30 is immediately adjacent to the opening or its bottom edge 38 is offset from the opening by about 1, 2, 3, 4, 5, 6, 7, 8, 9, 10 mm or more. In some embodiments, the bottom edge 38 of the second reinforcing member 30 is offset from the opening by about 1, 2, 3, 4, 5, 6, 7, 8, 9, 10, 11, 12, 13, 14, 15, 16, 17, 18, 19, 20 mm or more. In some embodiments, the bottom edge 38 of the second reinforcing member 30 is offset from the opening by about 1 mm. In some embodiments, the bottom edge 38 of the second reinforcing member 30 is offset from the opening by about 2 mm. In some embodiments, the bottom edge 38 of the second reinforcing member 30 is offset from the opening by about 3 mm. In some embodiments, the bottom edge 38 of the second reinforcing member 30 is offset from the opening by about 4 mm. In some embodiments, the bottom edge 38 of the second reinforcing member 30 is offset from the opening by about 5 mm. In some embodiments, the bottom edge 38 of the second reinforcing member 30 is offset from the opening by about 6 mm. In some embodiments, the bottom edge 38 of the second reinforcing member 30 is offset from the opening by about 7 mm. In some embodiments, the bottom edge 38 of the second reinforcing member 30 is offset from the opening by about 8 mm. In some embodiments, the bottom edge 38 of the second reinforcing member 30 is offset from the opening by about 9 mm. In some embodiments, the bottom edge 38 of the second reinforcing member 30 is offset from the opening by about 10 mm. In some embodiments, the bottom edge 38 of the second reinforcing member 30 is offset from the opening by more than about 10 mm. In some embodiments, the bottom edge 38 of the second reinforcing member 30 is offset from the opening by about 1-5 mm. In some embodiments, the bottom edge 38 of the second reinforcing member 30 is offset from the opening by about 1-10 mm. In some embodiments, the bottom edge 38 of the second reinforcing member 30 is offset from the opening by about 1-15 mm. In some embodiments, the bottom edge 38 of the second reinforcing member 30 is offset from the opening by about 1-20 mm. In some embodiments, the bottom edge 38 of the second reinforcing member 30 is offset from the opening by about 3-10 mm. In some embodiments, the bottom edge 38 of the second reinforcing member 30 is offset from the opening by about 3-15 mm. In some embodiments, the bottom edge 38 of the second reinforcing member 30 is offset from the opening by about 3-20 mm. In some embodiments, the bottom edge 38 of the second reinforcing member 30 is offset from the opening by about 5-10 mm. In some embodiments, the bottom edge 38 of the second reinforcing member 30 is offset from the opening by about 5-15 mm. In some embodiments, the bottom edge 38 of the second reinforcing member 30 is offset from the opening by about 5-20 mm. In some embodiments, the bottom edge 38 of the second reinforcing member 30 is offset from the opening by about 10-15 mm. In some embodiments, the bottom edge 38 of the second reinforcing member 30 is offset from the opening by about 10-20 mm.

In some embodiments, the length of the first reinforcing member 29 essentially extends the entire width of the opening 8. In some embodiments, the length of the second reinforcing member 30 essentially extends the entire width of the opening 8. In some embodiments, lengths of both the first reinforcing member 29 and the second reinforcing member 30 essentially extend the entire width of the opening 8. In some embodiments, the length of the first reinforcing member 29 essentially extends across the entire width of the opening 8 and the length of the second reinforcing member 30 essentially extends only partially across the width of the opening 8. In preferred embodiments, the length of the first reinforcing member 29 essentially extends the entire width of the opening 8. In preferred embodiments, the length of the second reinforcing member 30 essentially extends only partially across the width of the opening 8.

In some embodiments, both the first reinforcing member 29 and the second reinforcing member 30 are the same length. In some embodiments, the first reinforcing member 29 is about 5, 10, 15, 20, 25, 30, 35, 40, 45, 50, 55 mm, 60 mm, 65 mm, 70 mm, 75 mm, 80 mm, 85 mm, or any increment thereof, long. In some embodiments, the first reinforcing member 29 is about 5-55 mm long. In some embodiments, the first reinforcing member 29 is about 5-85 mm long. In some embodiments, the first reinforcing member 29 is about 5-80 mm long. In some embodiments, the first reinforcing member 29 is about 5-70 mm long. In some embodiments, the first reinforcing member 29 is about 5-60 mm long. In some embodiments, the first reinforcing member 29 is about 5-50 mm long. In some embodiments, the first reinforcing member 29 is about 5-40 mm long. In some embodiments, the first reinforcing member 29 is about 5-40 mm long. In some embodiments, the first reinforcing member 29 is about 5-30 mm long. In some embodiments, the first reinforcing member 29 is about 5-20 mm long. In some embodiments, the first reinforcing member 29 is about 5-10 mm long. In some embodiments, the first reinforcing member 29 is about 75-80 mm long.

In some embodiments, the second reinforcing member 30 is about 5, 10, 15, 20, 25, 30, 35, 40, 45, 50, 55 mm, 60 mm, 65 mm, 70 mm, 75 mm, 80 mm, 85 mm, or any increment thereof, long. In some embodiments, the second reinforcing member 30 is about 5-85 mm long. In some embodiments, the second reinforcing member 30 is about 5-80 mm long. In some embodiments, the second reinforcing member 30 is about 5-70 mm long. In some embodiments, the second reinforcing member 30 is about 5-60 mm long. In some embodiments, the second reinforcing member 30 is about 5-50 mm long. In some embodiments, the second reinforcing member 30 is about 5-40 mm long. In some embodiments, the second reinforcing member 30 is about 5-40 mm long. In some embodiments, the second reinforcing member 30 is about 5-30 mm long. In some embodiments, the second reinforcing member 30 is about 5-20 mm long. In some embodiments, the second reinforcing member 30 is about 5-10 mm long. In some embodiments, the second reinforcing member 30 is about 75-80 mm long.

In some embodiments, the lengths of the first (29) and second (30) reinforcing members are correlated with preventing incidences of leak from the medical device disclosed herein when it is in a closed condition. For example, the probability of an incidence of leak is about 10% to about 25% less in a medical device where first (29) and second (30) reinforcing members are 80 mm long than in a medical device where the first (29) and second (30) reinforcing members are 50 mm long.

In some embodiments, the first reinforcing member 29 is about 2, 3, 4, 5, 6, 7, 8, 9, 10, 11, 12, 13, 14, 15, 16, 17, 18, 19, or 20 mm wide. In some embodiments, the first reinforcing member 29 is about 2-20 mm wide. In some embodiments, the first reinforcing member 29 is about 5-20 mm wide. In some embodiments, the first reinforcing member 29 is about 10-20 mm wide. In some embodiments, the second reinforcing member 30 is about 2, 3, 4, 5, 6, 7, 8, 9, 10, 11, 12, 13, 14, 15, 16, 17, 18, 19, or 20 mm wide. In some embodiments, the second reinforcing member 30 is about 2-20 mm wide. In some embodiments, the second reinforcing member 30 is about 5-20 mm wide. In some embodiments, the second reinforcing member 10 is about 10-20 mm wide.

In some embodiments, the widths of the first 29 and second 30 reinforcing members are dependent on the type of material used for the reinforcing members. In some embodiments, the widths of the first 29 and second 30 reinforcing members are proportional to their flexibility. In some embodiments, the first reinforcing member 29 and the second reinforcing member 30 are made of polystyrene and are about 20 mm wide. In some embodiments, the first reinforcing member 29 and the second reinforcing member 30 are made of polyethylene and are about 15 mm wide. In preferred embodiments, the first reinforcing member 29 and the second reinforcing member 30 are made of polystyrene.

Figure 10:
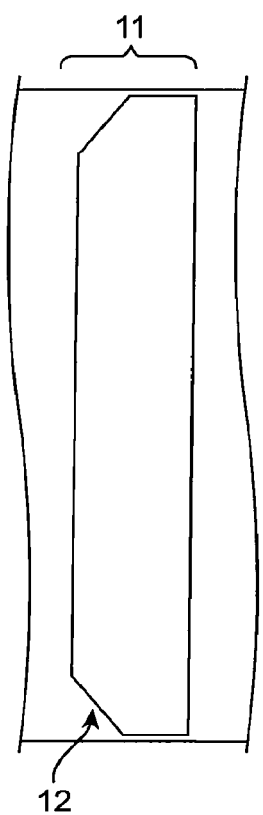
FIG. 10 shows an alternative shape for a reinforcing member of the ostomy pouch.

Referring to FIGS. 5 and 6, which illustrate a second embodiment of the medical device with an opening system, the first reinforcing member 29 and the second reinforcing member 30 have lateral edges 11. The lateral edges are deformable by application of pressure. The first reinforcing member 29 and the second reinforcing member 30 may have corners that are notched, square, rounded, flared, or have material removed, creating a void 12 (FIGS. 5 and 6), to facilitate finger positioning by a user. The material removed can be wedge shaped 12 (FIGS. 5 and 6) or triangular 32 (FIG. 10). The material can be removed from either a single lateral edge or from both lateral edges. The reinforcing member may have corners that are grooved, cut-to-shape or the like to allow finger positioning by a user.

The first or second embodiment of the medical device with an opening system may further comprise a securing system for securing the opening in the closed condition. In some embodiments, the securing system has a first fastener 13, attached to an exterior wall of the medical device or pouch; and a security flap 14. The first fastener 13 and the security flap 14 may be attached to opposing walls of the medical device or pouch 1. In some embodiments, the security flap 14 is attached to the front wall 2 and the first fastener 13 is directly attached to the rear wall 3, as shown in FIGS. 3 and 4, respectively. In these embodiments, the bottom edge of the first fastener 13 is immediately adjacent to or offset relative to the top edge of the first reinforcing member 9. In certain embodiments, the bottom edge of the first fastener 13 is immediately adjacent to the top edge of the first reinforcing member 9. In these embodiments, the bottom edge of the first fastener 13 is offset relative to the top edge of the first reinforcing member 9 by about 1, 2, 3, 4, 5, 6, 7, 8, 9, 10, 11, 12, 13, 14, 15, 16, 17, 18, 19, 20, 25, 30, 35, 40, 45, 50 mm or more, or any increment thereof. In these embodiments, the bottom edge of the first fastener 13 is offset relative to the top edge of the first reinforcing member 9 by about 1-100 mm. In these embodiments, the bottom edge of the first fastener 13 is offset relative to the top edge of the first reinforcing member 9 by about 1-50 mm. In these embodiments, the bottom edge of the first fastener 13 is offset relative to the top edge of the first reinforcing member 9 by about 1-20 mm. In these embodiments, the bottom edge of the first fastener 13 is offset relative to the top edge of the first reinforcing member 9 by about 1-10 mm. In some embodiments, the security flap 14 is attached to the front wall 2 and the first fastener 13 is attached to the first reinforcing member 29 located on the rear wall 3, as shown in FIGS. 5 and 6, respectively. As illustrated in the first embodiment shown in FIG. 8, the security flap 14 comprises a first portion 15 attached to one of the opposing walls of the medical device or pouch, on the outlet 7, and a second portion 16 freely extended outward from the same opposing wall of the medical device or pouch 1, on the outlet 7. The security flap 14 may be provided on the front wall 2 of the medical device or pouch 1, as shown in FIGS. 3, 5 and 8. The security flap 14 may be fastened to the front wall 2, for example by welding or by adhesive, or it may be an extension of a layer or portion forming the front wall 2. In the embodiment illustrated in FIG. 7, the freely extended portion 16 of security flap 14 is configured to be folded over the outlet 7 when the outlet is in the closed condition.

The securing system may further comprise a second fastener 17, wherein the second fastener is attached to the freely extended portion 16 of the security flap, as shown in FIG. 8. In some embodiments, as illustrated in FIGS. 7 and 9, the freely extended portion 16 of the security flap 14 is folded over the outlet 7 when the outlet is in the closed condition, and secured by the formation of a linkage between the first fastener 13 and second fastener 17. The first fastener 13 and the second fastener 17 are able to form a linkage after at least two lateral folds as shown in FIGS. 7 and 9. In the second embodiment of the medical device with an opening system, the freely extended portion 16 of the security flap 14 is folded over the outlet 7 when the outlet is in the closed condition, by forming a linkage between the first fastener 13 and second fastener 17 (not shown).

In the first embodiment of the medical device with an opening system, the first fastener 13 on the rear wall 3 may be approximately in register with the second reinforcing member 10 on the front wall 2.

In some embodiments, the security flap 14 prevents the outlet 7 from dropping down to its draining position (i.e., opened condition) while the security flap 14 is in its fastened condition. In some embodiments, the security flap comprises a semi-rigid or elasticized material capable of maintaining its shape after repeated closure. In some embodiments, the security flap comprises a memory foam-like material. In yet other embodiments, the security flap comprises film. In some other embodiments, the security flap comprises a fabric. In some embodiments, the fabric is a woven fabric or a non-woven fabric.

The first and second fasteners may be hook-and-loop fasteners, hook-and-pile fasteners, touch fasteners, adhesive couplings, molded couplings, formed couplings, snap closures, or hook and hook fasteners. Velcro™ is an exemplary hook and loop fastener. In some embodiments, the first and second fasteners are hook-and-loop fasteners. In some embodiments, the first and second fasteners are hook-and-pile fasteners. In some embodiments, the first and second fasteners are touch fasteners. In some embodiments, the first and second fasteners are adhesive couplings. In some embodiments, the first and second fasteners are molded couplings. In some embodiments, the first and second fasteners are formed couplings. In some embodiments, the first and second fasteners are snap closures. In some embodiments, the first and second fasteners are hook and hook fasteners. In certain embodiments, any of the fasteners re fixed directly to the pouch. In certain embodiments, any of the fasteners are fixed to one of the reinforcing members. In certain embodiments, the any of the fasteners itself serves as a reinforcing member.

Figure 12:
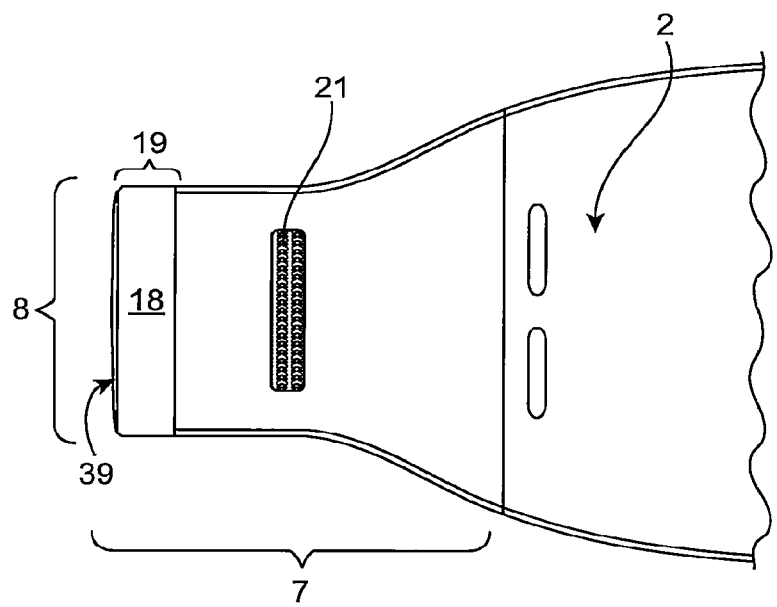
FIG. 12 shows a schematic front view of an alternative embodiment of the ostomy pouch with detail of the outlet in an open condition.
Figure 13:
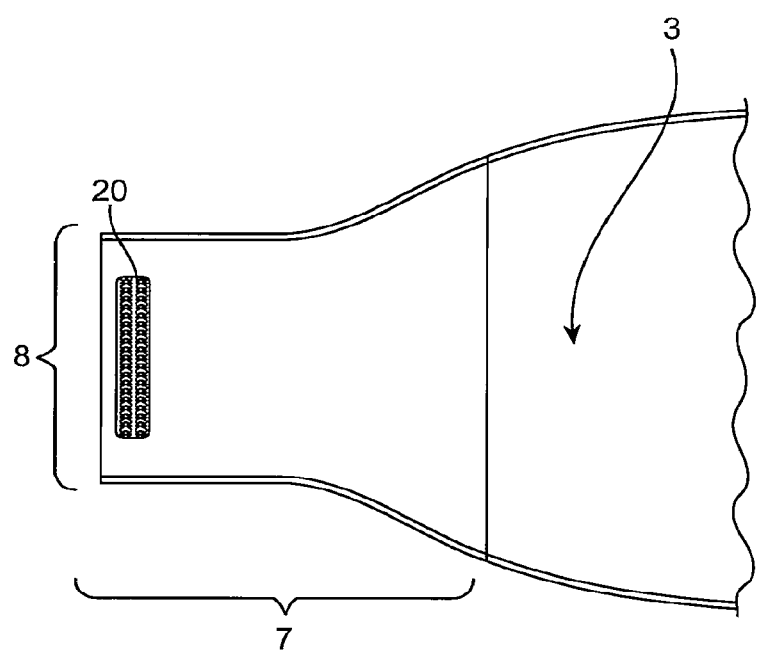
FIG. 13 shows a schematic rear view of an alternative embodiment of the ostomy pouch with detail of the outlet in an open condition.
Figure 14:
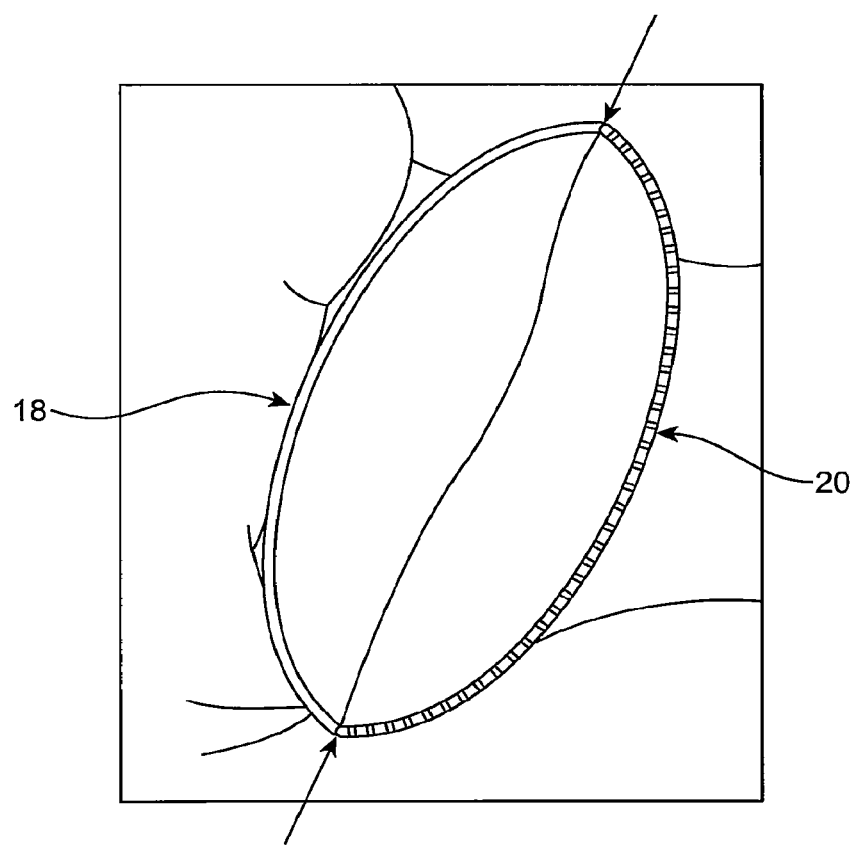
FIG. 14 shows the first reinforcing member of an alternative embodiment in a radially distended condition after the manual application of pressure.

FIGS. 12, 13 and 14 are exemplary of a third embodiment of the medical device with an opening system. This embodiment has a single reinforcing member 18 attached to an exterior surface of the device near the opening 8. The single reinforcing member 18 may be immediately adjacent to the opening, as shown in FIG. 12. In other embodiments, the bottom edge 39 of the single reinforcing member 18 may be offset from the opening by about 1, 2, 3, 4, 5, 6, 7, 8, 9, 10, 11, 12, 13, 14, 15, 16, 17, 18, 19, 20 mm or more. In some embodiments, the bottom edge 39 of the single reinforcing member 18 is offset from the opening by about 1 mm. In some embodiments, the bottom edge 39 of the single reinforcing member 18 is offset from the opening by about 2 mm. In some embodiments, the bottom edge 39 of the single reinforcing member 18 is offset from the opening by about 3 mm. In some embodiments, the bottom edge 39 of the single reinforcing member 18 is offset from the opening by about 4 mm. In some embodiments, the bottom edge 39 of the single reinforcing member 18 is offset from the opening by about 5 mm. In some embodiments, the bottom edge 39 of the single reinforcing member 18 is offset from the opening by about 6 mm. In some embodiments, the bottom edge 39 of the single reinforcing member 18 is offset from the opening by about 7 mm. In some embodiments, the bottom edge 39 of the single reinforcing member 18 is offset from the opening by about 8 mm. In some embodiments, the bottom edge 39 of the single reinforcing member 18 is offset from the opening by about 9 mm. In some embodiments, the bottom edge 39 of the single reinforcing member 18 is offset from the opening by about 10 mm. In some embodiments, the bottom edge 39 of the single reinforcing member 18 is offset from the opening by more than about 10 mm. In some embodiments, the bottom edge 39 of the single reinforcing member 18 is offset from the opening by about 1-5 mm. In some embodiments, the bottom edge 39 of the single reinforcing member 18 is offset from the opening by about 1-10 mm. In some embodiments, the bottom edge 39 of the single reinforcing member 18 is offset from the opening by about 1-15 mm. In some embodiments, the bottom edge 39 of the single reinforcing member 18 is offset from the opening by about 1-20 mm. In some embodiments, the bottom edge 39 of the single reinforcing member 18 is offset from the opening by about 3-10 mm. In some embodiments, the bottom edge 39 of the single reinforcing member 18 is offset from the opening by about 3-15 mm. In some embodiments, the bottom edge 39 of the single reinforcing member 18 is offset from the opening by about 3-20 mm. In some embodiments, the bottom edge 39 of the single reinforcing member 18 is offset from the opening by about 5-10 mm. In some embodiments, the bottom edge 39 of the single reinforcing member 18 is offset from the opening by about 5-15 mm. In some embodiments, the bottom edge 39 of the single reinforcing member 18 is offset from the opening by about 5-20 mm. In some embodiments, the bottom edge 39 of the single reinforcing member 18 is offset from the opening by about 10-15 mm. In some embodiments, the bottom edge 39 of the single reinforcing member 18 is offset from the opening by about 10-20 mm.

As shown in FIG. 12, in some embodiments, the single reinforcing member 18 essentially extends the entire width of the opening 8. In other embodiments, the single reinforcing member 18 essentially extends only partially across the width of the opening 8. In some embodiments, the single reinforcing member 18 is about 5, 10, 15, 20, 25, 30, 35, 40, 45, 50, 55 mm, 60 mm, 65 mm, 70 mm, 75 mm, 80 mm, or 85 mm, or any increment thereof, long. In some embodiments, the single reinforcing member 18 is about 5-85 mm long. In some embodiments, the single reinforcing member 18 is about 5-80 mm long. In some embodiments, the single reinforcing member 18 is about 5-60 mm long. In some embodiments, the single reinforcing member 18 is about 5-70 mm long. In some embodiments, the single reinforcing member 18 is about 5-50 mm long. In some embodiments, the single reinforcing member 18 is about 5-40 mm long. In some embodiments, the single reinforcing member 18 is about 5-25 mm long. In some embodiments, the single reinforcing member 18 is about 5-30 mm long. In some embodiments, the single reinforcing member 18 is about 5-20 mm long. In some embodiments, the single reinforcing member 18 is about 5-10 mm long. In some embodiments, the single reinforcing member 18 is about 75-80 mm long.

In some embodiments, the single reinforcing member 18 has lateral edges 19. The reinforcing member 18 is deformable by the application of manual pressure to its lateral edges, optionally in the direction of the arrows from its flat un-deformed state to a curved deformed state as shown in FIG. 14. As a result, the outlet opening distends radially under the pressure. Such deformation is reversible when the pressure is removed.

The reinforcing member may have corners that are notched, square, rounded, flared or have material removed, creating a void, to facilitate finger positioning by a user. The material removed can be wedge shaped or triangular. The reinforcing member may have corners that are grooved, cut-to-shape or the like to allow finger positioning by a user.

The third embodiment of the medical device with an opening system may further comprise a first fastener 20 and a second fastener 21, attached to opposing exterior surfaces on the walls, as shown in FIGS. 12 and 13. The first fastener 20 may be opposite the single reinforcing member 18. In some embodiments, the horizontal and/or vertical centerlines of both the single reinforcing member 18 and the first fastener 20 are aligned with one another. In some embodiments, the horizontal and/or vertical centerlines of the single reinforcing member 18 and the first fastener 20 are offset relative to one another by about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 mm or more. More preferably, the horizontal and/or vertical centerlines of the single reinforcing member 18 and the first fastener 20 may be offset relative to each other by about 0, 1, 2, 3, 4, 5, 6, 7, 8, 9, 10 mm or more. Most preferably, the single reinforcing member 18 and the first fastener 20 may be vertically and/or horizontally offset relative to each other by about 0, 1, 2, 3, 4, 5 mm or more.

In some embodiments, as shown in FIG. 12, the second fastener 21 is opposite the first fastener 20 and distal to the opening 8 with respect to the single reinforcing member 18. In some embodiments, the horizontal centerline of second fastener 21 is offset relative to the horizontal centerline of the single reinforcing member 18 by about 20, 25, 30, 35, 40, 45, 50, 55, 60, 65, 70, 75, 80, 85, 90, 95, or 100 mm, or increments thereof. In some embodiments, the horizontal centerline of second fastener 21 is offset relative to the horizontal centerline of the single reinforcing member 18 by about 20-100 mm. In some embodiments, the horizontal centerline of second fastener 21 is offset relative to the horizontal centerline of the single reinforcing member 18 by about 20-90 mm. In some embodiments, the horizontal centerline of second fastener 21 is offset relative to the horizontal centerline of the single reinforcing member 18 by about 20-80 mm. In some embodiments, the horizontal centerline of second fastener 21 is offset relative to the horizontal centerline of the single reinforcing member 18 by about 20-70 mm. In some embodiments, the horizontal centerline of second fastener 21 is offset relative to the horizontal centerline of the single reinforcing member 18 by about 20-60 mm. In some embodiments, the horizontal centerline of second fastener 21 is offset relative to the horizontal centerline of the single reinforcing member 18 by about 20-50 mm.

In some embodiments, the first fastener 20 and the second fastener 21 are hook-and-loop fasteners, hook-and-pile fasteners, or touch fasteners, adhesive coupling, molded couplings, formed couplings, snap closures, or hook and hook fasteners. Velcro™ is an exemplary hook and loop fastener. In some embodiments, the first fastener 20 and the second fastener 21 are hook-and-loop fasteners. In some embodiments, the first fastener 20 and the second fastener 21 are hook-and-pile fasteners. In some embodiments, the first fastener 20 and the second fastener 21 are touch fasteners. In some embodiments, the first fastener 20 and the second fastener 21 are adhesive couplings. In some embodiments, the first fastener 20 and the second fastener 21 are molded couplings. In some embodiments, the first fastener 20 and the second fastener 21 are formed couplings. In some embodiments, the first fastener 20 and the second fastener 21 are snap closures. In some embodiments, the first fastener 20 and the second fastener 21 are hook and hook fasteners. The first fastener 20 may lie directly on top of, and be attached to, a second reinforcing member (not shown). In this third embodiment, the first fastener 20 and second fastener 21 can form a linkage after at least two lateral folds of the outlet 7.

The aforementioned third embodiment may also have a securing system The securing system consists of a third fastener (not shown) attached to one exterior wall, and a security flap (not shown) attached to an exterior surface of the outlet with one end extending freely, having a fourth fastener. The fourth fastener may be able to form a linkage with the third fastener after at least two lateral folds of the outlet. In certain embodiments, the outlet requires a single lateral fold. In certain embodiments, the outlet requires two lateral folds to be in a closed condition. In certain embodiments, the outlet requires three lateral folds to be in a closed condition. In certain embodiments, the outlet requires four lateral folds to be in a closed condition. In certain embodiments, the outlet requires five lateral folds to be in a closed condition. The lateral folds are carried out in an upward direction with respect to the opening 8 such that the outlet 7 is folded from an open to a closed condition. In some embodiments, the third and the fourth fastener form a linkage after three lateral folds of the outlet. In some embodiments, the third and the fourth fastener form a linkage after four lateral folds of the outlet. In some embodiments, the third and the fourth fastener form a linkage after five lateral folds of the outlet.

In any of the above mentioned embodiments, the medical device with an opening system further comprises one or more support members (not shown), distinct from the reinforcing members in that they do not essentially extend for the entire width of the opening. These supports can aid in the radial distension of the opening (not shown). In some embodiments, the support members are made of the same material as the reinforcing member. In some embodiments, the support members are made of a different material than the reinforcing member. In some embodiments, the support members are about 5, 10, 15, 20, 25, 30, 35, 40, 45, 50, 55 mm, 60 mm, 65 mm, or 70 mm, or any increment thereof, long. In some embodiments, the support members are about 5-70 mm long. In some embodiments, the support members are about 5-65 mm long. In some embodiments, the support members are about 5-60 mm long. In some embodiments, the support members are about 5-55 mm long. In some embodiments, the support members are about 5-50 mm long. In some embodiments, the support members are about 5-50 mm long. In some embodiments, the support members are about 5-40 mm long. In some embodiments, the support members are about 5-30 mm long. In some embodiments, the support members are about 5-20 mm long. In some embodiments, the support members are about 5-10 mm long.

In some embodiments, the length of the support members is 5-20% less than the length of the reinforcing members. In some embodiments, the length of the support members is about 5% less than the length of the reinforcing members. In some embodiments, the length of the support members is about 10% less than the length of the reinforcing members. In some embodiments, the length of the support members is about 15% less than the length of the reinforcing members. In some embodiments, the length of the support members is about 20% less than the length of the reinforcing members.

In some embodiments, the one or more support members are attached to the front wall 2. In some embodiments, the one or more support members, are positioned between the second reinforcing member 10 and the security flap 14. In some embodiments, the one or more support members are attached to the front wall 2. In some embodiments, the one or more support members, are positioned within the outlet, above the first reinforcing member 9.

Figure 15:
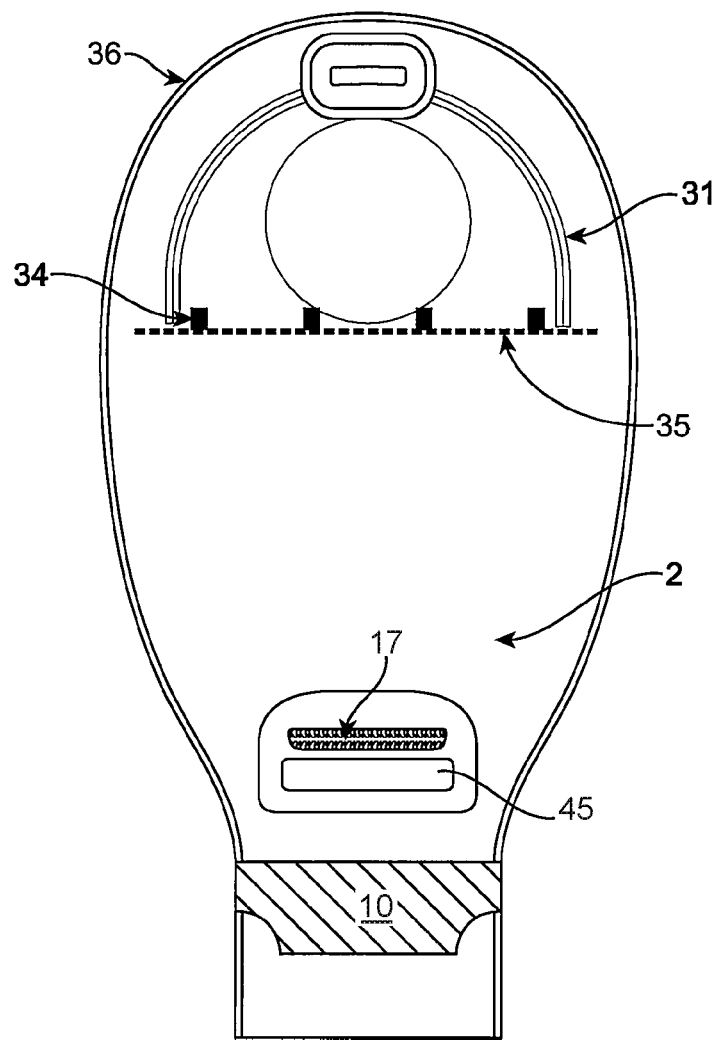
FIG. 15 shows a schematic front view of an embodiment of the ostomy pouch containing a flap attached to the inner wall of the front wall.

In any of the aforementioned embodiments, the medical device with an opening system further includes a flap 31 present between the front wall 2 and the rear wall 3, as illustrated in FIG. 15. In some embodiments, the flap 31 is welded to the front wall 2. In some embodiments, the flap 31 has a partially free edge portion that is attached intermittently 34 to the inner surface of the front wall 2 and has openings 35 that permit odorous gas to reach the filter assembly 22 for deodorization while deterring a ballooning of the pouch 1 due to captured gas within the pouch. In some embodiments, the flap 31 essentially extends partially down from the top edge 36 of the medical device or pouch 1 so as to at least partially and preferably totally cover and protect the filter assembly 22 from any body waste material entering the medical device or pouch 1 through the stomal aperture 4. In some embodiments, the top edge of the flap 31 is about 5 mm, about 10 mm, about 15 mm, about 20 mm, or about 25 mm, or any increments thereof, below the top edge 36 of the medical device or pouch 1. In some embodiments, the top edge of the flap 31 is about 5-25 mm below the top edge 36 of the medical device or pouch 1. In some embodiments, the top edge of the flap 31 is about 5-20 mm below the top edge 36 of the medical device or pouch 1. In some embodiments, the top edge of the flap 31 is about 5-15 mm below the top edge 36 of the medical device or pouch 1. In some embodiments, the top edge of the flap 31 is about 5-10 mm below the top edge 36 of the medical device or pouch 1. In some embodiments, the top edge of the flap 31 is about 15-20 mm below the top edge 36 of the medical device or pouch 1. In some embodiments, the partially free edge portion 32 of the flap is welded to the inner wall of the front wall 2 by one or more spot welds. In some embodiments, the partially free edge portion of the flap is welded to the inner wall of the front wall 2 by four spot welds.

This disclosure also provides for methods of manufacture of the medical device or pouch with an opening system. Components can be positioned onto a substrate by hand in a sequential process using fixtures. A manual or automated web process can be used in conjunction with automatic dispensing, pick and place or other automatic transport to position the components onto a substrate. The components can be attached to the substrate by bonding, sealing or adhesive attachment.

What is claimed is:

1. A medical device, comprising:
a first wall and a second wall joined to the first wall such that a cavity is formed between the first wall and the second wall, the cavity having an outlet opening formed at a proximal end of the medical device;
a first deformable reinforcing member attached to the first wall, wherein the first deformable reinforcing member is deformable by manual application of pressure to lateral edges of the first deformable reinforcing member so as to radially distend the outlet opening, wherein the first deformable reinforcing member includes at least one first notch formed in at least one lateral edge thereof, and wherein each notch is configured to receive a portion of a user's digit to facilitate manual application of pressure to said lateral edges.

2. The medical device of claim 1, further comprising a first fastener and a second fastener operable to engage the first fastener to secure the medical device in a closed condition.

3. The medical device of claim 1, wherein the first deformable reinforcing member is attached to an exterior surface of the first wall.

4. The medical device of claim 1, wherein the at least one notch comprises a pair of first notches; and
wherein the pair of first notches are formed on opposite lateral edges.

5. The medical device of claim 1, wherein the at least one notch is formed in a corner of the first deformable reinforcing member.

6. The medical device of claim 1, further comprising a second deformable reinforcing member attached to the second wall, wherein the second deformable reinforcing member comprises at least one second notch formed in at least one lateral edge thereof.

7. The medical device of claim 1, wherein the medical device is an ostomy pouch.

8. A medical device, comprising:
a pair of walls joined to one another such that a cavity is formed between the pair of walls, wherein the pair of walls define an outlet region comprising an outlet opening formed at one end of the medical device;
at least one deformable reinforcing member positioned in the outlet region, wherein each deformable reinforcing member is deformable by manual application of pressure to lateral edges thereof so as to radially distend the outlet opening, wherein each deformable reinforcing member includes a notch formed in a first lateral edge thereof, and wherein each notch is sized and shaped to receive a portion of a manual digit to facilitate manual application of pressure to the lateral edges.

9. The medical device of claim 8, wherein each deformable reinforcing member is attached to a corresponding wall of the pair of walls.

10. The medical device of claim 8, wherein the at least one deformable reinforcing member comprises a pair of the deformable reinforcing members.

11. The medical device of claim 10, wherein the pair of deformable reinforcing members are longitudinally offset from one another.

12. The medical device of claim 11, wherein the notches of the pair of deformable reinforcing members face each other and are operable to simultaneously receive a single manual digit.

13. The medical device of claim 10, wherein the pair of deformable reinforcing members are attached to opposite walls of the pair of walls.

14. The medical device of claim 8, further comprising a pair of fasteners capable of forming a linkage to retain the medical device in a closed condition.

15. The medical device of claim 8, wherein the medical device is an ostomy pouch.

16. A medical device, comprising:
a pouch defining a cavity, the pouch including an outlet region defining an outlet opening;
a deformable reinforcing member coupled to the outlet region, wherein the deformable reinforcing member is configured to deform in response to application of pressure to opposite lateral edges thereof to thereby distend the outlet opening, and wherein at least one of the lateral edges includes a notch sized and shaped to receive a portion of a manual digit to facilitate manual application of pressure to the lateral edges.

17. The medical device of claim 16, wherein each lateral edge of the deformable reinforcing member comprises a corresponding and respective notch.

18. The medical device of claim 16, wherein the deformable reinforcing member is coupled to an exterior of the outlet region.

19. The medical device of claim 16, wherein each of the lateral edges includes a corresponding and respective notch.

20. The medical device of claim 16, wherein the medical device is an ostomy pouch.

* * * * *